(12) United States Patent
Thierbach et al.

(10) Patent No.: US 10,683,511 B2
(45) Date of Patent: Jun. 16, 2020

(54) METHOD FOR THE FERMENTATIVE PRODUCTION OF L-AMINO ACIDS

(71) Applicant: EVONIK DEGUSSA GMBH, Essen (DE)

(72) Inventors: Georg Thierbach, Bielefeld (DE); Thomas Bekel, Halle (DE); Kornelia Voss, Halle (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/132,827

(22) Filed: Sep. 17, 2018

(65) Prior Publication Data

US 2019/0085340 A1    Mar. 21, 2019

(30) Foreign Application Priority Data

Sep. 18, 2017 (EP) .................................... 17191616

(51) Int. Cl.
| | |
|---|---|
| *C12N 15/70* | (2006.01) |
| *C12P 13/08* | (2006.01) |
| *C12P 13/24* | (2006.01) |
| *C07K 14/34* | (2006.01) |
| *C12P 13/12* | (2006.01) |

(52) U.S. Cl.
CPC .............. *C12N 15/70* (2013.01); *C07K 14/34* (2013.01); *C12P 13/08* (2013.01); *C12P 13/12* (2013.01); *C12P 13/24* (2013.01)

(58) Field of Classification Search
None
See application file for complete search history.

(56) References Cited

U.S. PATENT DOCUMENTS

| | | | |
|---|---|---|---|
| 5,688,671 | A | 11/1997 | Sugimoto |
| 6,844,176 | B1 | 1/2005 | Bathe et al. |
| 6,893,848 | B1 | 5/2005 | Yokoi et al. |
| 7,332,309 | B2 | 2/2008 | Rieping |
| 7,338,790 | B2 | 3/2008 | Thierbach et al. |
| 8,697,850 | B2 | 4/2014 | Jessberger et al. |
| 9,422,568 | B2 | 8/2016 | Jessberger et al. |
| 2004/0115816 | A1 | 6/2004 | Pompejus et al. |
| 2004/0171160 | A1 | 9/2004 | Pompejus et al. |
| 2005/0196848 | A1 | 9/2005 | Dusch et al. |
| 2010/0240131 | A1 | 9/2010 | Pompejus et al. |
| 2017/0051324 | A1 | 2/2017 | Ochrombel et al. |
| 2018/0363014 | A1 | 12/2018 | Voss et al. |
| 2019/0106721 | A1 | 4/2019 | Bekel et al. |

FOREIGN PATENT DOCUMENTS

| | | |
|---|---|---|
| EP | 0 841 395 | 5/1998 |
| EP | 1 108 790 | 6/2001 |
| EP | 1 239 040 | 9/2002 |
| EP | 3 141 597 | 3/2017 |
| EP | 3 144 383 | 3/2017 |
| WO | WO 01/00804 | 1/2001 |
| WO | WO 2008/033001 | 3/2008 |

OTHER PUBLICATIONS

U.S. Appl. No. 16/149,285, filed Oct. 2, 2018, now US-2019/0106721 A1, dated Apr. 11, 2019, Bekel.
European Search Report and Opinion for corresponding application EP 17 19 1616 completed Oct. 18, 2017.
European Search Report for corresponding application EP 18 19 4968 completed Nov. 7, 2018.
Blombach, et al., "Acetohydroxyacid Synthase, a Novel Target for Improvement of L-Lysine Production by *Corynebacterium glutamicum*," *Applied and Environmental Microbiology* 75(2):419-427 (Jan. 2009).
Ikeda and Nakagawa, "The *Corynebacterium glutamicum* genome: features and impacts on biotechnological process," *Applied Microbiology and Biotechnology* 62(2-3):99-109 (Aug. 2003).
Jäger, et al., "A *Corynebacterium glutamicum* Gene Conferring Multidrug Resistance in the Heterologous Host *Escherichia coli*," *Journal of Bacteriology* 179(7):2449-2451 (Apr. 1997).
Larkin, et al., "Clustral W and Clustral X Version 2.0" *Bioinformatics* 23(21):2947-2948 (Nov. 2007).
Lv, et al., "Genome Sequence of *Corynebacterium glutamicum* ATCC 14067, Which Provides Insight into Amino Acid Biosynthesis in Corneform Bacteria," *Journal of Bacteriology* 194(3):742-743 (Feb. 2012).
Peters-Wendisch, et al., "Pyruvate carboxylase from *Corynebacterium glutamicum*: characterization, expression and inactivation of the pyc gene," *Microbiology* 144(4):915-927 (Apr. 1998).
Schäfer, et al., "Small mobilizable multi-purpose cloning vectors derived from *Escherichia coli* plasmids pK18 and pK19: selection of defined deletions in the chromosome of *Corynebacterium glutamicum*," *Gene* 145(1):69-73 (Jul. 1994).
Schwarzer and Pühler, "Manipulation of *Corynebacterium glutamicum* by gene disruption and replacement," *Bio/Technology* 9:84-87 (1991).
Tang, et al., "The optimization of preparations of competent cells for transformation of *E. coli*," *Nucleic Acids Research* 22(14):2857-2858 (Jul. 1994).
Tosaka, et al., "L-Lysine Production by S-(2-Aminoethyl) L-Cysteine and α-Amino-β-hydroxyvarelic Acid Resistant Mutants of *Brevibacterium lactofermentum*," *Agriculture and Biological Chemistry* 42(2):745-752 (1978).
Wendisch, et al., "Updates on industrial production of amino acids using *Corynebacterium glutamicum*," *World J Microbiol Biotechnol* 32: 105 :1-10 (Apr. 2016).

(Continued)

*Primary Examiner* — Suzanne M Noakes
(74) *Attorney, Agent, or Firm* — Law Office of: Michael A. Sanzo, LLC

(57) ABSTRACT

The present invention provides a bacterium of the genus *Corynebacterium*, in particular of the species *Corynebacterium glutamicum*, having the ability to excrete an L-amino acid selected from proteinogenic L-amino acids and L-omithine and new measures for the fermentative production of proteinogenic L-amino acids and L-ornithine by such bacteria.

16 Claims, No Drawings
Specification includes a Sequence Listing.

(56) References Cited

OTHER PUBLICATIONS

Yukawa, et al., "Comparative analysis of the *Corynebacterium glutamicum* group and complete genome sequence of strain R," *Microbiology* 153(4):1042-1058 (Apr. 2007).
GenBank Accession No. AGQQ02000001; locus tag KIQ 001800; protein ID KEI24322; submitted Aug. 31, 2011.
GenBank Accession No. ANU34683; submitted Dec. 11, 2015.
GenBank Accession No. AP009044, nts 2959048-2960427; protein ID BAF55689; submitted Aug. 10, 2005.
GenBank Accession No. AP009044; sequence ID BAF55440; submitted Aug. 10, 2005.
GenBank Accession No. AX066329; protein ID CAC26403 from WO0100804 filed Jan. 4, 2001.
GenBank Accession No. BAF55440; submitted Aug. 10, 2005.
GenBank Accession No. BAF55689; submitted Aug. 10, 2005.
GenBank Accession No. BAV24403; submitted Jun. 10, 2016.
GenBank Accession No. CP016335; locus tag BBD29_13545; submitted Dec. 11, 2015.
GenBank Accession No. KEI24322; submitted Aug. 31, 2011.
GenBank Accession No. NC_003450; protein ID NP601971; gene ID 1020721; submitted Sep. 23, 2002.
NCBI Reference Sequence: NP_601971; submitted May 24, 2002.
NCBI Reference Sequence: NZ_CP016335; locus tag BBD29_13545; protein ID WP060565255; submitted Dec. 11, 2005.
GenBank Accession No. U43535; protein ID AAB51443; submitted Dec. 18, 1995.
NCBI Reference Sequence: WP_060565255; submitted Oct. 28, 2018.
U.S. Appl. No. 16/007,523, filed Jun. 13, 2018, 2018-0363014 A1, dated Dec. 20, 2018, Voss.
U.S. Appl. No. 16/219,718, filed Dec. 13, 2018, Voss.

METHOD FOR THE FERMENTATIVE PRODUCTION OF L-AMINO ACIDS

CROSS REFERENCE TO RELATED APPLICATIONS

The present application claims priority to European application 17191616.6, filed on Sep. 18, 2017, the contents of which is incorporated by reference herein in its entirety.

FIELD OF THE INVENTION

The present invention provides a bacterium of the genus *Corynebacterium*, in particular of the species *Corynebacterium glutamicum*, having the ability to excrete an L-amino acid selected from proteinogenic L-amino acids and L-omithine and new measures for the fermentative production of proteinogenic L-amino acids and L-ornithine by such bacteria.

BACKGROUND OF THE INVENTION

L-Amino acids are used in human medicine, in the pharmaceutical industry, in the food industry and particularly in nutrition of animals.

L-amino acids such as, for example, L-lysine, are produced by fermentation of strains of the genus *Corynebacterium*, in particular *Corynebacterium glutamicum*. Because of its great economic importance, work is continually being done on improving the production methods. Improvements may relate to fermentation technology such as, e.g., stirring and supplying oxygen, or to the composition of the nutrient media, e.g., the sugar concentration during fermentation, or to the processing of the fermentation broth to a suitable product form by, e.g., drying and granulating the fermentation broth or ion exchange chromatography or may relate to the intrinsic performance properties of the microorganism itself.

The methods used for improving the performance properties of these microorganisms are those of mutagenesis, selection and screening of mutants. The strains obtained in this way are resistant to anti-metabolites or are auxotrophic for metabolites of regulatory importance, and produce L-amino acids. A known anti-metabolite is the L-lysine analogue S-(2-aminoethyl)-L-cysteine (see e.g., Tosaka, et al., Agricultural and Biological Chemistry 42(4), 745-752, (1978)).

Methods of recombinant DNA technology have likewise been used for a number of years for strain improvement of L-amino acid-producing strains of the genus *Corynebacterium* by modifying, i.e. enhancing or attenuating, individual L-amino acid biosynthesis genes and investigating the effect on L-amino acid production. Wendisch, et al. provide a review about amino acid production in *C. glutamicum* (World J Microbiol Biotechnol (2016) 32:105, 1-10).

Lee, et al. teach that the inactivation of a gene encoding a secretory protein results in an increase of L-lysine production in *C. glutamicum* (EP 3 141 597 A1). EP 3 144 383 A1 discloses that the inactivation of an intrinsic oxaloacetate decarboxylase enhances the L-lysine production in *C. glutamicum*. Möckel, et al. disclose that the attenuation of the poxB gene in *C. glutamicum* increases the production of L-lysine (EP 1 096 013 A2).

Ochrombel, et al. teach that the introduction of a glycine cleavage system into *C. glutamicum* increases the production of L-amino acids (EP 2 940 039 A1).

The nucleotide sequences of the chromosomes of various bacteria or strains resp. of the genus *Corynebacterium* and of the species *Corynebacterium glutamicum*, and their analysis have been disclosed. This information is available at publicly accessible databases and may be used for strain development purposes. One such data base is the GenBank data base of the NCBI (National Center for Biotechnology Information, U.S. National Library of Medicine 8600 Rockville Pike, Bethesda Md., 20894 USA).

During the annotation and submission procedure for a sequenced chromosome identified structures such as, e.g., genes or coding sequences are furnished with a unique identifier called locus_tag by the supplier of the information to the data base.

*Corynebacterium glutamicum* contains a gene in its chromosome which has an activity of conferring resistance to different drugs in *Escherichia coli*.

Jäger, et al. (Journal of Bacteriology, 179(7), 2449-2451 (1997)) identified a gene termed cmr (corynebacterial multidrug resistance) in the chromosome of *Corynebacterium glutamicum* ATCC13032 which mediates resistance to several structurally unrelated antibiotics such as erythromycin, tetracycline, puromycin and bleomycin in *Escherichia coli*. This cmr gene confers a resistance phenotype only to *Escherichia coli*, but not to *Corynebacterium glutamicum*. Based on amino acid sequence analysis Jäger, et al. concluded that the gene encodes a hydrophobic protein with 12 potential transmembrane-spanning α-helical segments showing similarity to drug-$H^+$ antiporters. Jäger, et al. further stated that the protein has a structure common for transport proteins belonging to the major facilitator family. However, the function of the activity of this protein in *Corynebacterium glutamicum* is still unknown. The nucleotide sequence of the cmr gene and the amino acid sequence of the encoded polypeptide are available under GenBank accession number U43535. The amino acid sequence of the encoded polypeptide is also shown under SEQ ID NO:1 of the sequence listing.

The nucleotide sequence of the *Corynebacterium glutamicum* ATCC13032 chromosome and its analysis was described by Ikeda and Nakagawa (Applied Microbiology and Biotechnology 62, 99-109(2003)) and in EP 1 108 790 A2. It is available at the NCBI under accession number NC_003450. Locus_tag NCgl2680 identifies a sequence coding for a "multidrug resistance protein". EP 1 108 790 A2 also discloses nucleotide sequences coding for fragments of this multidrug resistance protein.

Nakagawa discloses under GenBank accession number NP_601971 the encoded amino acid sequence of a polypeptide defined as "multidrug resistance protein" of *Corynebacterium glutamicum* of ATCC13032. It is also shown under SEQ ID NO:2 of the sequence listing.

WO 2001/000804 A2 discloses various genes encoding stress, resistance and tolerance proteins (SRT proteins) from *Corynebacterium glutamicum* ATCC13032 and their use for the modulation of production of fine chemicals. Under identification code RXA01666 (page 59) and SEQ ID NO:233 and SEQ ID NO:234 a nucleotide sequence and the amino acid sequence of the encoded protein having the function of a multidrug resistance protein are disclosed. These sequences are also disclosed under GenBank accession number AX066329. It is stated that SRT proteins may be overexpressed (p37) or disrupted (p44). However, a specific application of said nucleotide sequence for the production of a specific fine chemical is not disclosed.

The amino acid sequences of entries U43535 and NP_601971 were compared and found to be identical over their full length. The two amino acid sequences were also found to be identical with the amino acid sequence of the multidrug resistance protein of ATCC13032 as disclosed in SEQ ID NO:234 of WO 2001/000804 A2 (see also GenBank accession number AX066329). Nishio, et al. disclose under GenBank accession number BAV24403 the encoded amino acid sequence of a protein defined as "permeases of the major facilitator superfamily" of a *Corynebacterium glutamicum* ssp. *lactofermentum* strain referred to as AJ1511. It is also shown under SEQ ID NO:3 of the sequence listing.

The nucleotide sequence of the chromosome of *Corynebacterium glutamicum* ATCC13869, a strain formerly referred to as *Brevibacterium lactofermentum*, and its analysis were disclosed by Chen, et al. at the NCBI under accession number NZ_CP016335. Locus_tag BBD29_RS13550 identifies a sequence coding for an "MFS transporter". Chen, et al. disclose under GenBank accession number ANU34683 the encoded amino acid sequence of a protein defined as "multidrug transporter" of *Corynebacterium glutamicum* ATCC13869 (formerly referred to as *Brevibacterium lactofermentum*). It is also shown under SEQ ID NO:4 of the sequence listing.

The amino acid sequences of entries BAV24403 and ANU34683 were compared and found to be identical over the full length. When compared to the amino acid sequence of the corresponding polypeptide of ATCC13032 the identity was found to be 99.3%.

The nucleotide sequence of the *Corynebacterium glutamicum* R chromosome and its analysis were described by Yukawa, et al. (Microbiology 153(4):1042-1058 (2007)). It is available at the NCBI under accession number AP009044. Locus_tag_cgR_2674 identifies a sequence coding for a hypothetical protein comprising a region named "MFS". "MFS" is the abbreviation for "Major Facilitator Superfamily". Yukawa, et al. disclose under GenBank accession number BAF55689 the encoded amino acid sequence of a protein from *Corynebacterium glutamicum* R having a region named "MFS". It is also shown under SEQ ID NO:5 of the sequence listing. Its identity to the corresponding amino acid sequence from ATCC13032 was found to be 98.9%.

The term "MFS" is the abbreviation for "Major Facilitator Superfamily". According to the conserved domain database at the NCBI (see database entry cd06174) the term denotes a large and diverse group of secondary transporters that includes uniporters, symporters, and antiporters, which facilitate the transport across cytoplasmic or internal membranes of a variety of substrates including ions, sugar phosphates, drugs, neurotransmitters, nucleosides, amino acids, and peptides. Lv, et al. (Journal of Bacteriology 194(3), 742-743 (2012)) describe the sequencing and analysis of the chromosome of *Corynebacterium glutamicum* ATCC14067, a strain formerly referred to as *Brevibacterium flavum*. It is available at the NCBI under accession number AGQQ02000001 and AGQQ02000002. Locus_tag KIQ_001800 identifies a sequence coding for a "multidrug transporter". Lv et al. disclose under GenBank accession number KEI24322 the encoded amino acid sequence of a protein from *Corynebacterium glutamicum* ATCC14067 (formerly referred to as *Brevibacterium flavum*) defined as a "multidrug transporter" having a region named "MFS". It is also shown under SEQ ID NO:6 of the sequence listing. Its identity to the corresponding amino acid sequence from ATCC13032 was found to be 99.6%.

A summary of the findings is shown in table 1.

TABLE 1

Comparison of the encoded amino acid sequences of Cmr polypeptides of various strains of *Corynebacterium glutamicum* with the encoded amino acid sequence of the Cmr polypeptide of ATCC13032 (GenBank accession number NP_601971; see also SEQ ID NO: 2) by sequence alignment using the software program Clustal W (Larkin, et al., Clustal W and Clustal X version 2.0. In: Bioinformatics 23, 2947-2948 (2007)).

| *Corynebacterium glutamicum* Strain | Accession Number | Length (number of amino acid residues) | Identical amino acids | % Identity | Sequence (SEQ ID NO:) |
|---|---|---|---|---|---|
| ATCC13032 | U43535 | 459 | 459 | 100.0 | SEQ ID NO: 1 |
| AJ1511 | BAV24403 | 459 | 456 | 99.3 | SEQ ID NO: 3 |
| ATCC13869 | ANU34683 | 459 | 456 | 99.3 | SEQ ID NO: 4 |
| R | BAF55689 | 459 | 454 | 98.9 | SEQ ID NO: 5 |
| ATCC14067 | KEI24322 | 459 | 457 | 99.6 | SEQ ID NO: 6 |

The amino acid sequence of the encoded Cmr polypeptide from ATCC 13032 shown in SEQ ID NO: 2 is also shown in SEQ ID NO:8.

SUMMARY OF THE INVENTION

An object of the present invention is to provide new measures for the fermentative production of proteinogenic L-amino acids and L-ornithine by bacteria of the genus *Corynebacterium*, preferably of the species *Corynebacterium glutamicum*.

It was found that the production of proteinogenic L-amino acids and/or L-ornithine by bacteria of the genus *Corynebacterium* in which the activity of the Cmr polypeptide the function of which is still unknown in *Corynebacterium glutamicum* is eliminated e.g. by modifying the polynucleotide coding for said Cmr polypeptide and which are cultivated in a suitable medium under suitable fermentation conditions is improved with respect to the amount of product formed and/or production rate of product as compared to the unmodified bacterium.

Therefore, the present invention provides a bacterium of the genus *Corynebacterium* having the ability to excrete an L-amino acid selected from proteinogenic L-amino acids and L-ornithine, wherein within the chromosome of said bacterium a polynucleotide encoding a polypeptide, which is at least 90% identical to the amino acid sequence of SEQ ID NO:8 and which confers upon *Escherichia coli* a resistance to at least one antibiotic, selected from erythromycin, tetracycline, puromycin and bleomycin, is modified by deleting at least a part of the coding sequence for the Cmr polypeptide corresponding to the amino acids of positions 149 to 251, 41 to 344, or 14 to 435 of the amino acid sequence according to SEQ ID NO:8 or by deleting at least the complete nucleotide sequence coding for said polypeptide, preferably by deleting the complete coding sequence and the adjoining stop codon.

DETAILED DESCRIPTION OF THE INVENTION

The polypeptide, which confers upon *Escherichia coli* a resistance to at least one antibiotic, selected from erythromycin, tetracycline, puromycin and bleomycin, is also referred to as Cmr polypeptide (corynebacterial multi drug resistance polypeptide) herewith. Teachings for measuring resistance/sensitivity phenotypes can be found in text books of medical microbiology such the textbook of H. Brandis, W. Köhler, H. J. Eggers and G. Pulverer (Lehrbuch der Medizinischen Mikrobiologie, 7th edition, Gustav Fischer Verlag, 1994) and by Jäger, et al. (Journal of Bacteriology, 179(7), 2449-2451 (1997)).

Erythromycin is a macrolide antibiotic produced by *Saccharopolyspora erythraea*. The CAS (Chemical Abstracts Service) registry number is 114-07-8.

Tetracycline is a polyketide antibiotic produced by *Streptomyces* species. The CAS registry number is 60-54-8. The CAS registry number of the corresponding HCl salt is 64-75-5.

Puromycin is a nucleoside antibiotic produced by *Streptomyces alboniger*. The CAS registry number is 53-79-2. The CAS registry number of the corresponding dihydrochloride salt is 58-58-2.

Bleomycin is a glycopeptide antitumor antibiotic produced by *Streptomyces verticillus*. The CAS registry number is 11056-06-7. The CAS registry number of the corresponding $H_2SO_4$ salt is 9041-93-4.

Summaries concerning antibiotics may be found, inter alia, in the text book of Jason C. Gallagher and Conan MacDougall (Antibiotics Simplified, $2^{nd}$ edition, Jones & Bartlett Learning, 2012).

The polypeptide the activity of which is eliminated by modifying the polynucleotide coding for said polypeptide in the *Corynebacterium* according to the present invention confers upon *Escherichia coli* a resistance preferably to the antibiotics erythromycin and/or tetracycline.

Proteinogenic L-amino acids are to be understood to mean the L-amino acids present in natural proteins, that is proteins of microorganisms, plants, animals and humans. Proteinogenic L-amino acids comprise L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline and in some cases L-selenocysteine and L-pyrrolysine.

The term L-amino acids, where mentioned herein, in particular in the context of product formation, also comprises their ionic forms and salts, for example L-lysine monohydrochloride or L-lysine sulfate in the case of the L-amino acid L-lysine.

The amino acid sequence of said encoded Cmr polypeptide the activity of which is eliminated by modifying the polynucleotide coding for said polypeptide in the *Corynebacterium* according to the present invention comprises 459 amino acid residues prior to the modification of the polynucleotide. It is known in the art that the N-terminal amino acid methionine of an encoded polypeptide may be removed by an aminopeptidase during or after translation (Jocelyn E. Krebs, Elliott S. Goldstein and Stephan T. Kilpatrick: Lewin's Genes X, Jones and Bartlett Publishers, US, 2011).

The amino acid sequence of the encoded Cmr polypeptide from ATCC13032 shown in SEQ ID NO:2 is also shown in SEQ ID NO:8. The nucleotide sequence encoding said polypeptide is shown in SEQ ID NO:7 positions 1001 to 2377.

In the *Corynebacterium* according to the present invention the polypeptide the activity of which is eliminated by modifying the polynucleotide coding for said polypeptide comprises the amino acid sequence of SEQ ID NO:8 or SEQ ID NO:10 or SEQ ID NO:12, preferably said polypeptide comprises the amino acid sequence of SEQ ID NO:8 prior to the modification of the polynucleotide.

During the work for the present invention the coding sequence for the Cmr polypeptide of strain DSM13994 (deposited at DSMZ, Braunschweig, Germany on 16 Jan. 2001) described in EP 1 239 040 A2 was analyzed. Said coding sequence of strain DSM13994 was found to be identical with that of strain ATCC13032 with the exception of position 1341. Position 1341 of the coding sequence corresponds to position 2341 of SEQ ID NO:7. Position 1341 of the coding sequence in DSM13994 contains the nucleobase thymine (t) resulting in a get codon. Position 1341 of the coding sequence in ATCC13032 contains cytosine (c) resulting in a gcc codon. Both codons code for L-alanine.

The amino acid sequence of the encoded Cmr polypeptide from ATCC13869 shown in SEQ ID NO:4 is also shown in SEQ ID NO:10. The nucleotide sequence encoding said polypeptide is shown in SEQ ID NO:9 positions 1001 to 2377.

The amino acid sequence of the encoded Cmr polypeptide from ATCC14067 shown in SEQ ID NO:6 is also shown in SEQ ID NO:12. The nucleotide sequence encoding said polypeptide is shown in SEQ ID NO:11 positions 1001 to 2377.

Prior to the modification of the polynucleotide the nucleotide sequence encoding said Cmr polypeptide is preferably selected from SEQ ID NO:7 positions 1001 to 2377, SEQ ID NO:7 positions 1001 to 2377, wherein at position 2341 thymine (t) is contained, SEQ ID NO:9 positions 1001 to 2377 and SEQ ID NO:11 positions 1001 to 2377, with SEQ ID NO:7 positions 1001 to 2377 and SEQ ID NO:7 positions 1001 to 2377, wherein at position 2341 thymine (t) is contained, being particularly preferred.

In the *Corynebacterium* the polynucleotide that is modified according to the present invention and that is coding for said Cmr polypeptide comprises the positions 1001 to 2377 of the nucleotide sequence of SEQ ID NO:7 or the positions 1001 to 2377 of SEQ ID NO:7, wherein at position 2341 cytosine (c) is replaced by thymine (t).

Teachings and information concerning the handling of and experimental work with polynucleotides may be found, inter alia, in the handbook of J. Sambrook, et al. (Molecular Cloning, A Laboratory Manual, Cold Spring Harbor Laboratory Press, 1989), the textbook of C. R. Newton and A. Graham (PCR, Spektrum Akademischer Verlag, 1994) and the handbook of D. Rickwood and B. D. Hames (Gel electrophoresis of nucleic acids, a practical approach, IRL Press, 1982).

For sequence analysis of polynucleotides and polypeptides, e.g. sequence alignments, public software such as the CLC Genomics Workbench (Qiagen, Hilden, Germany) or the program MUSCLE provided by the European Bioinformatics Institute (EMBL-EBI, Hinxton, UK) may also be used.

During the work for the present invention it was found that modifying L-amino acid excreting bacteria of the genus *Corynebacterium*, preferably of the species *Corynebacterium glutamicum*, by eliminating the activity of Cmr polypeptide by modifying the polynucleotide coding for said polypeptide increased their ability to excrete L-amino acids as compared to the unmodified bacterium.

The skilled artisan is aware from a number of methods of mutagenesis how to achieve said eliminating, or switching off resp., of said Cmr polypeptide in the *Corynebacterium*.

As a consequence of said elimination by deleting, novel junction points, or junction sites resp., are created in the chromosome of the *Corynebacterium*, preferably *Corynebacterium glutamicum*.

If, for example, the complete coding sequence including the adjoining stop codon is deleted a novel junction point is created in the chromosome of the *Corynebacterium glutamicum* which links the first nucleobase after the stop codon of the coding sequence, e.g., the nucleobase at position 2381 of SEQ ID NO:7, SEQ ID NO:7 containing thymine (t) at position 2341, SEQ ID NO:9 or SEQ ID NO:11, with the first nucleobase preceding the start codon of the coding sequence, e.g., the nucleobase at position 1000 of SEQ ID NO:7, SEQ ID NO:9 or SEQ ID NO:11.

In a specific embodiment of the present invention the nucleotide sequence from positions 1001 to 2380 of SEQ ID NO:7, SEQ ID NO:7 containing thymine (t) at position 2341, SEQ ID NO:9 or SEQ ID NO:11, preferably SEQ ID NO:7 or SEQ ID NO:7 containing thymine (t) at position 2341, which comprises the coding sequence of the Cmr polypeptide including the adjoining stop codon, is deleted and the nucleotide sequence gatatc, which is the recognition site for the restriction endonuclease EcoRV inserted into the site of deletion. Thus, the modification of the nucleotide sequence encoding the Cmr polypeptide within the chromosome of the *Corynebacterium* results in an insertion of a recognition site for the restriction enzyme EcoRV.

Accordingly, a novel junction site is created herewith in the chromosome of the *Corynebacterium* characterized by the gatatc nucleotide sequence bridge between the nucleobase c at position 1000 and the nucleobase g at position 2381 of SEQ ID NO:7, SEQ ID NO:7 containing thymine (t) at position 2341, SEQ ID NO:9 or SEQ ID NO:11, preferably SEQ ID NO:7 or SEQ ID NO:7 containing thymine (t) at position 2341.

The nucleotide sequence of the novel junction site created including the nucleotide sequences upstream and downstream therefrom are shown in SEQ ID NO:13 and tables 2 and 3.

TABLE 2

List of nucleotide sequences indicating a deletion of the complete coding sequence for the Cmr polypeptide and the adjoining stop codon accompanied by the insertion of the recognition site for the restriction enzyme EcoRV in strains of the species *Corynebacterium glutamicum* in accordance with the present invention. The nucleotide sequence of the recognition site for the restriction endonuclease EcoRV extends from position 801 to 806 in SEQ ID NO: 13.

| line | nucleotide sequence | length* |
|---|---|---|
| a | SEQ ID NO: 13 positions 796 to 807 | 12 |
| b | SEQ ID NO: 13 positions 795 to 807 | 13 |
| c | SEQ ID NO: 13 positions 794 to 807 | 14 |
| d | SEQ ID NO: 13 positions 793 to 807 | 15 |
| e | SEQ ID NO: 13 positions 792 to 807 | 16 |
| f | SEQ ID NO: 13 positions 791 to 807 | 17 |

*length in nucleobases or base pairs resp.

TABLE 3

List of nucleotide sequences indicating a deletion of the complete coding sequence for the Cmr polypeptide and the adjoining stop codon accompanied by the insertion of the recognition site for the restriction enzyme EcoRV in strains of the species *Corynebacterium glutamicum* in accordance with the present invention. The nucleotide sequence of the recognition site for the restriction endonuclease EcoRV extends from position 801 to 806 in SEQ ID NO: 13.

| line | nucleotide sequence | length* |
|---|---|---|
| a | SEQ ID NO: 13 positions 798 to 808 | 11 |
| b | SEQ ID NO: 13 positions 797 to 808 | 12 |
| c | SEQ ID NO: 13 positions 796 to 808 | 13 |
| d | SEQ ID NO: 13 positions 795 to 808 | 14 |
| e | SEQ ID NO: 13 positions 794 to 808 | 15 |
| f | SEQ ID NO: 13 positions 793 to 808 | 16 |

*length in nucleobases or base pairs resp.

Accordingly, in a more specific embodiment of the present invention a deletion of the complete coding sequence for the Cmr polypeptide and the adjoining stop codon accompanied by the insertion of the recognition site for the restriction enzyme EcoRV in the chromosome of a *Corynebacterium*, in particular of a *Corynebacterium glutamicum*, preferably ATCC13032, ATCC13869, ATCC14067 and L-amino acid excreting strains obtained from these strains is identified by one of the nucleotide sequences shown in tables 2 and 3.

A common method for incorporating mutations into chromosomal genes of *Corynebacterium glutamicum* is the method of gene replacement described by Schwarzer and Pühler (Bio/Technology 9, 84-87 (1991)) and further elaborated by Schäfer et al. (Gene 145, 69-73 (1994)). Peters-Wendisch et al. (Microbiology 144, 915-927 (1998)) used the gene replacement method to inactivate the pyc gene of *Corynebacterium glutamicum* encoding pyruvate carboxylase. Schafer et al. used the method to incorporate a deletion into the hom-thrB gene region of *Corynebacterium glutamicum*. In EP1094111 the method was used to incorporate a deletion into the pck gene of *Corynebacterium glutamicum* encoding phosphoenol pyruvate carboxykinase.

In the gene replacement method, a mutation, such as, for example, a deletion, insertion or substitution of at least one nucleobase, is constructed in vitro in the nucleotide sequence of the gene in question.

In the context of the present invention the gene in question is the cmr gene. The nucleotide sequence of the cmr gene contains a coding sequence for a polypeptide having an activity of conferring resistance in *Escherichia coli* to at least one antibiotic, selected from erythromycin, tetracycline, puromycin and bleomycin, as specified in this invention. Examples of such nucleotide sequences are SEQ ID NO:7, SEQ ID NO:7 containing thymine (t) at position 2341, SEQ ID NO:9 and SEQ ID NO:11 of the sequence listing. In the context of the present invention the mutation preferably is a deletion located in the coding sequence of said cmr gene.

The mutated nucleotide sequence of the gene in question comprises i) a nucleotide sequence at the 5'-end of the site of mutation, which is also referred to as 5'-flanking sequence or upstream sequence in the art, ii) a nucleotide sequence at the 3'-end of the site of mutation, which is also referred to as 3'-flanking sequence or downstream sequence in the art, and iii) the nucleotide sequence of the site of mutation between i) and ii). The site of mutation is in the context of the present invention characterized by a lack of a specific sequence, namely a deletion in or of the coding sequence for the Cmr polypeptide, and accordingly also characterized by the sequences flanking the site of mutation (flanking sequences).

For some applications it may be convenient to further incorporate a suitable polynucleotide into said site of mutation. Said suitable polynucleotide may inter alia contain the coding sequence for an enzyme of the biosynthetic pathway of an L-amino acid, e. g. the coding sequence for the enzyme aspartokinase, which is an enzyme of the L-lysine biosynthetic pathway, or the nucleotide sequence of the recognition site for a restriction enzyme useful for further strain improvement.

An example of a mutated nucleotide sequence in the context of the present invention is shown in SEQ ID NO:13. The 5'-flanking sequence consists of the nucleotide sequence from positions 201 to 1000 of SEQ ID NO:7. The 3'-flanking sequence consists of the nucleotide sequence from positions 2381 to 3180 of SEQ ID NO:7. The nucleotide sequence from positions 1001 to 2380 of SEQ ID NO:7 that comprises the coding sequence for the Cmr polypeptide and the adjoining stop codon was removed and the nucleotide sequence of the recognition site of the restriction endonuclease EcoRV incorporated as shown from positions 801 to 806 of SEQ ID NO:13.

The mutated nucleotide sequence constructed is cloned into a suitable plasmid vector that is not capable of autonomous replication in *Corynebacterium*, preferably *Corynebacterium glutamicum*. Suitable plasmid vectors, preferably plasmid vectors enabling gene replacement, are pK*mob and pK*mobsacB, particularly preferred pK18mobsacB, described by Schäfer et al. (Gene 145, 69-73, 1994). These plasmid vectors are capable of autonomous replication in *Escherichia coli* but not in *Corynebacterium*. However due to their mobilizable nature they can be transferred from *Escherichia coli* to *Corynebacterium* by conjugation. Due to the presence of the sacB gene selection system, conferring sucrose sensitivity to its host, plasmid vector pK18mobsacB provides the means to select for double recombination events after homologous recombination. It thus enables the isolation of strains carrying the desired mutation in the gene of interest. Similar plasmid vectors are described in e. g. WO2002070685 A2 and WO2003014362 A2.

This plasmid vector containing the mutated nucleotide sequence is subsequently transferred into the desired strain of *Corynebacterium*, e.g. *Corynebacterium glutamicum* strain DM1933 (i.e., DSM25442; Blombach, et al., Applied and Environmental Microbiology 75(2), 419-427, 2009), by transformation or conjugation. After two events of homologous recombination comprising a recombination event within the 5'-flanking sequence provided by the plasmid vector with the homologous sequence of the *Corynebacterium glutamicum* chromosome and a recombination event within the 3'-flanking sequence provided by the plasmid vector with the homologous sequence of the *Corynebacterium glutamicum* chromosome, one effecting integration and one effecting excision of said plasmid vector, the mutation is incorporated in the *Corynebacterium glutamicum* chromosome. In this way the nucleotide sequence of the gene in question contained in the chromosome of said desired strain is replaced by the mutated nucleotide sequence. An event of homologous recombination may also be referred to as crossing over.

For practicing the present invention bacteria of the genus *Corynebacterium* are used. A description of the genus *Corynebacterium* and the species comprised by this genus can be found in the article "*Corynebacterium*" by K. A. Bernard and G. Funke in Bergey's Manual of Systematics of Archaea and Bacteria (Bergey's Manual Trust, 2012). The bacterium of the genus *Corynebacterium* according to the present invention preferably belongs to the species *Corynebacterium glutamicum*.

The *Corynebacterium* according to the present invention has the ability to excrete proteinogenic L-amino acids, selected from L-lysine, L-valine, L-threonine, L-isoleucine, L-histidine and L-proline, and L-ornithine.

Suitable strains of *Corynebacterium glutamicum* are wild strains of this species for example strains ATCC13032, ATCC14067 and ATCC13869, and L-amino acid excreting strains obtained from these wild strains, preferably L-amino acid excreting strains obtained from these wild strains.

Strain ATCC13032 (also available as DSM20300) is the taxonomic type strain of the species *Corynebacterium glutamicum*. Strain ATCC14067 (also available as DSM20411) is also known under the outdated designation *Brevibacterium flavum*. Strain ATCC13869 (also available as DSM1412) is also known under the outdated designation *Brevibacterium lactofermentum*. A taxonomic study of this group of bacteria based on DNA-DNA hybridization was done by Liebl et al. (International Journal of Systematic Bacteriology 41(2), 255-260, 1991). A comparative analysis of various strains of the species *Corynebacterium glutamicum* based on genome sequence analysis was provided by Yang and Yang (BMC Genomics 18(1):940).

A multitude of L-amino acid excreting strains of the genus *Corynebacterium*, in particular from the species *Corynebacterium glutamicum*, were obtained in the art during the past decades starting from strains such as ATCC13032, ATCC14067, ATCC13869 and the like. They were obtained as a result of strain development programs targeted at the desired L-amino acid(s) using inter alia methods like classical mutagenesis, selection for antimetabolite resistance as well as amplification and promotor modification of genes of the biosynthetic pathway of the L-amino acid in question by genetic engineering methods. Summaries may be found in L. Eggeling and M. Bott (Handbook of *Corynebacterium glutamicum*, CRC Press, 2005) or H. Yukawa and M. Inui (*Corynebacterium glutamicum* Biology and Biotechnology, Springer Verlag, 2013). L-lysine excreting strains of the species *Corynebacterium glutamicum* are widely known in the art and can be used for the purpose of the present invention. For example Blombach et al. (Applied and Environmental Microbiology 75(2), 419-427, 2009) describe a *Corynebacterium glutamicum* strain DM1933, which has been deposited under accession DSM25442 according to the Budapest treaty. Furthermore L-lysine excreting *Corynebacterium glutamicum* strain DM2031, deposited according to the Budapest Treaty as DSM32514 may be used. Strain DM2031 is a further developed derivative of DM1933 having enhanced. L-lysine excretion ability. Other L-lysine excreting *Corynebacterium glutamicum* strains are e. g. described in WO2008033001 A1 and EP0841395 A1.

L-lysine excreting strains of the species *Corynebacterium glutamicum* typically contain a polynucleotide coding for a feedback resistant aspartokinase polypeptide variant. A feedback resistant aspartokinase polypeptide variant means an aspartokinase which is less sensitive, or desensitized resp., to inhibition by mixtures of L-lysine and L-threonine, e.g. 10 mM each, or mixtures of the L-lysine analogue S-(2-aminoethyl)-L-cysteine and L-threonine, e.g., 50 mM S-(2-aminoethyl)-L-cysteine and 10 mM L-threonine, when compared to the wild form of the enzyme, which is contained in wild strains like for example ATCC13032, ATCC14067 and ATCC13869. The EC number for aspartokinase is EC 2.7.2.4. Descriptions of polynucleotides of *Corynebacte-* rium glutamicum encoding a feedback resistant aspartokinase polypeptide variant are for example given in U.S. Pat. Nos. 5,688,671, 6,844,176 and 6,893,848. A summarizing list can be found inter alia in WO2009141330 A1.

Accordingly said L-lysine excreting strains of the species *Corynebacterium glutamicum* used for the measures of the present invention preferably contain at least one copy of a polynucleotide coding for a feedback resistant aspartokinase.

SEQ ID NO:14 shows the nucleotide sequence of the coding sequence of the aspartokinase polypeptide of strain ATCC13032 and SEQ ID NO:15 the amino acid sequence of the encoded polypeptide. It is known in the art (see U.S Pat. No. 6,893,848) that exchange of the amino acid Thr at position 311 of SEQ ID NO:15 for Ile imparts the enzyme feedback resistance to inhibition by mixtures of L-lysine and L-threonine.

Accordingly it is preferred that the amino acid sequence of said feedback resistant aspartokinase polypeptide comprises the amino acid sequence of SEQ ID NO:15 containing Isoleucin at position 311.

Said amino exchange can be achieved by exchanging the nucleobase cytosine (c) at position 932 of SEQ ID NO:14 to give thymine (t). The acc codon for threonine is thus altered to the atc codon for isoleucine.

It is further known in the art that exchange of the gtg start codon of the coding sequence for the aspartokinase polypeptide for atg enhances expression of the polypeptide (see e.g., EP2796555).

Accordingly it is preferred that the sequence coding for a feedback resistant aspartokinase polypeptide begins with an atg start codon.

Summaries concerning the breeding of L-lysine excreting strains of *Corynebacterium glutamicum* may be found, inter alia, in L. Eggeling and M. Bott (Handbook of *Corynebacterium glutamicum*, CRC Press, 2005), V. F. Wendisch (Amino Acid Biosynthesis—Pathways, Regulation and Metabolic Engineering, Springer Verlag, 2007), H. Yukawa and M. Inui (*Corynebacterium glutamicum* Biology and Biotechnolgy, Springer Verlag, 2013), and Eggeling and Bott (Applied Microbiology and Biotechnology 99 (9), 3387-3394, 2015).

L-threonine excreting strains of the species *Corynebacterium glutamicum* are known in the art and can be used for the purpose of the present invention. For example EP0385940 A1 describes strain DSM5399.

L-valine excreting strains of the species *Corynebacterium glutamicum* are known in the art and can be used for the purpose of the present invention. For example U.S Pat. No. 5,188,948 describes strain AJ12341, which is deposited under FERM BP-1763 and EP2811028 A1 describes strain ATCC14067_PprpD2-ilvBN.

L-isoleucine excreting strains of the species *Corynebacterium glutamicum* are known in the art and can be used for the purpose of the present invention. For example U.S Pat. No. 4,656,135 describes strain AJ12152, which is deposited under Ferm BP-760.

L-histidine excreting strains of the species *Corynebacterium glutamicum* are known in the art, for example in U.S Pat. No. 4,495,283, and can be used for the purpose of the present invention.

L-proline excreting strains of the species *Corynebacterium glutamicum* are known in the art and can be used for the purpose of the present invention. For example EP1828384 A1 describes an L-proline excreting *Corynebacterium glutamicum* strain comprising a polypeptide having γ-glutamyl kinase activity which contains at position 149 of the encoded amino acid sequence L-aspartic acid.

L-ornithine excreting strains of the species *Corynebacterium glutamicum* are known in the art and can be used for the purpose of the present invention. For example EP2553113 A2 describes L-ornithine excreting *Corynebacterium glutamicum* strain ATCC13032_ Delta_argFRGH and transformants derived from the strain.

In case a wild strain, e.g., ATCC13032, ATCC13869 or ATCC14067, is in a first step subjected to the measures of the present invention the resulting strain is in a second step subjected to a strain development program targeted at the desired L-amino acid to obtain a bacterium according to the present invention.

The L-amino acid excreting strains of *Corynebacterium*, preferably *Corynebacterium glutamicum*, of the present invention have the ability to excrete ≥0.1 g/l, preferably ≥0.25 g/l, particularly preferred ≥0.5 g/l of the desired L-amino acid in a suitable medium under suitable conditions.

Preferably, the secreted L-amino acid according to the present invention is L-lysine.

The invention further provides a method for the fermentative production of an L-amino acid, selected from proteinogenic L-amino acids, preferably L-lysine, L-valine, L-threonine, L-isoleucine, L-histidine and L-proline, and L-ornithine, preferably L-lysine, and L-ornithine, comprising the steps of
a) cultivating the bacterium of the genus the *Corynebacterium*, preferably *Corynebacterium glutamicum*, according to the present invention in a suitable medium under suitable conditions,
b) accumulating said L-amino acid in the medium to form an L-amino acid containing fermentation broth.

The method according to the present invention may further comprise the concentration of the L-amino acid containing fermentation broth. The L-amino acid containing fermentation broth or said concentrate obtained by a method according to the present invention is optionally further dried. In a further step, the L-amino acid can be purified from said L-amino acid containing fermentation broth or said concentrate or dried concentrate.

In a fermentative process according to the invention a *Corynebacterium*, preferably *Corynebacterium glutamicum*, modified in accordance with the present invention and having the ability to excrete an L-amino is cultivated in a suitable medium under suitable conditions. Due to said ability to excrete said L-amino acid the concentration of the L-amino acid increases and accumulates in the medium during the fermentative process and the L-amino acid is thus produced.

The fermentative process may be discontinuous process like a batch process or a fed batch process or a continuous process. A summary concerning the general nature of fermentation processes is available in the textbook by H. Chmiel (Bioprozesstechnik, Spektrum Akademischer Verlag, 2011), in the textbook of C. Ratledge and B. Kristiansen (Basic Biotechnology, Cambridge University Press, 2006) or in the textbook of V. C. Hass and R. Pörtner (Praxis der Bioprozesstechnik Spektrum Akademischer Verlag, 2011).

A suitable medium used for the production of an L-amino acid by a fermentative process contains a carbon source, a nitrogen source, a phosphorus source, inorganic ions and other organic compounds as required.

Suitable carbon sources include glucose, fructose, sucrose as well as the corresponding raw materials like starch hydrolysate, molasses or high fructose corn syrup.

As nitrogen source organic nitrogen-containing compounds such as peptones, meat extract, soy bean hydrolysates or urea, or inorganic compounds such as ammonium sulphate, ammonium chloride, ammonium phosphate, ammonium carbonate, ammonium nitrate, ammonium gas or aqueous ammonia can be used.

As phosphorus source, phosphoric acid, potassium dihydrogen phosphate or dipotassium hydrogen phosphate or the corresponding sodium-containing salts can be used. Inorganic ions like potassium, sodium, magnesium, calcium, iron and further trace elements etc. are supplied as salts of sulfuric acid, phosphoric acid or hydrochloric acid. Other organic compounds means essential growth factors like vitamins e. g. thiamine or biotin or L-amino acids, e.g. L-homoserine.

The media components may be added to the culture in form of a single batch or be fed in during the cultivation in a suitable manner.

During the fermentative process the pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8.0. To control foaming, it is possible to employ antifoam agents such as, for example, fatty acid polyglycol esters. To maintain the stability of plasmids, it is possible to add to the medium suitable selective substances such as, for example, antibiotics. The fermentative process is preferably carried out under aerobic conditions. In order to maintain these conditions, oxygen or oxygen-containing gas mixtures such as, for example air are introduced into the culture. The fermentative process is carried out, where appropriate, at elevated pressure, for example at an elevated pressure of 0.03 to 0.2 MPa. The temperature of the culture is normally from 25° C. to 40° C., preferably from 30° C. to 37° C. In a discontinuous process, the cultivation is continued until an amount of the desired L-amino acid sufficient for being recovered has been formed. The cultivation is then completed. This aim is normally achieved within 10 hours to 160 hours. In continuous processes, longer cultivation times are possible. Examples of suitable media and culture conditions can be found, inter alia, in L. Eggeling and M. Bott (Handbook of *Corynebacterium glutamicum*, CRC Press, 2005) and the patent documents U.S Pat. Nos. 5,770,409, 5,990, 350, 5,275,940, 5,763,230 and 6,025,169.

Thus the fermentative process results in a fermentation broth which contains the desired L-amino acid.

In the method according to the present invention the L-amino acid produced is selected from the proteinogenic L-amino acids L-lysine, L-valine, L-threonine, L-isoleucine, L-histidine and L-proline, and L-ornithine. Preferably, the L-amino acid produced is L-lysine.

A product containing the L-amino acid is then recovered in liquid or solid from the fermentation broth.

A "fermentation broth" means a medium in which a *Corynebacterium* of the invention has been cultivated for a certain time and under certain conditions.

When the fermentative process is completed, the resulting fermentation broth accordingly comprises:
 a) the biomass (cell mass) of the *Corynebacterium* of the invention, said biomass having been produced due to propagation of the cells of said *Corynebacterium*,
 b) the desired L-amino acid accumulated during the fermentative process,
 c) the organic by-products accumulated during the fermentative process, and
 d) the components of the medium employed which have not been consumed in the fermentative process.

The organic by-products include compounds which may be formed by the *Corynebacterium* of the invention during the fermentative process in addition to production of the desired L-amino acid.

The fermentation broth is removed from the culture vessel or fermentation tank, collected where appropriate, and used for providing a product containing the fine chemical, preferably an L-amino acid-containing product, in liquid or solid form. The expression "recovering the fine chemical-containing product" is also used for this. In the simplest case, the L-amino acid-containing fermentation broth itself, which has been removed from the fermentation tank, constitutes the recovered product.

The fermentation broth can subsequently be subjected to one or more of the measures selected from the group consisting of:
 a) partial (>0% to <80%) to complete (100%) or virtually complete (≥80%, ≥90%, ≥95%, ≥96%, ≥97%, ≥98%, ≥99%) removal of the water,
 b) partial (>0% to <80%) to complete (100%) or virtually complete (≥80%, ≥90%, ≥95%, ≥96%, ≥97%, ≥98%, ≥99%) removal of the biomass, the latter being optionally inactivated before removal,
 c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic by-products formed during the fermentative process, and
 d) partial (>0%) to complete (100%) or virtually complete (≥80%, ≥90%, ≥95%, ≥96%, ≥97%, >98%, ≥99%, ≥99.3%, ≥99.7%) removal of the residual components of the medium employed or of the residual input materials resp., which have not been consumed in the fermentative process.

An abundance of technical instructions for measures a), b), c) and d) are available in the art.

Removal of water (measure a)) can be achieved inter alia by evaporation, using, e.g., a falling film evaporator, by reverse osmosis or nano-filtration. The concentrates thus obtained can be further worked up by spray drying or spray granulation. It is likewise possible to dry the fermentation broth directly using spray drying or spray granulation.

Removal of the biomass (measure b) can be achieved inter alia by centrifugation, filtration or decantation or a combination thereof.

Removal of the organic by-products (measure c)) or removal of residual components of the medium (measure d) can be achieved inter alia by chromatography, e.g., ion exchange chromatography, treatment with activated carbon or crystallization. In case the organic by-products or residual components of the medium are present in the fermentation broth as solids they can be removed by measure b).

General instructions on separation, purification and granulation methods can be found inter alia in the book of R. Ghosh "Principles of Bioseperation Engineering" (World Scientific Publishing, 2006), the book of F. J. Dechow "Separation and Purification Techniques in Biotechnology" (Noyes Publications, 1989), the article "Bioseparation" of Shaeiwitz et al (Ullmann's Encyclopedia of Industrial Chemistry, Wiley-VCH, 2012) and the book of P. Serno et al. "Granulieren" (Editio Cantor Verlag, 2007).

A downstream processing scheme for L-lysine products can be found in the article "L-lysine Production" of R. Kelle et al. (L. Eggeling and M. Bott (Handbook of *Corynebacterium glutamicum*, CRC Press, 2005)). U.S Pat. No. 5,279, 744 teaches the manufacturing of a purified L-lysine product by ion exchange chromatography. U.S Pat. No. 4,956,471 teaches the manufacturing of a purified L-valine product by ion exchange chromatography. U.S Pat. No. 5,431,933 teaches the manufacturing of dry L-amino acid products, e. g. an L-lysine product or an L-valine product, containing most of the constituents of the fermentation broth.

Thus a concentration or purification of the desired L-amino acid is achieved and a product having the desired content of said L-amino acid is provided.

Analysis of L-amino acids to determine the concentration at one or more time(s) during the fermentation can take place by separating the L-amino acids by means of ion exchange chromatography, preferably cation exchange chromatography, with subsequent post-column derivatization using ninhydrin, as described in Spackman, et al. (Analytical Chemistry 30: 1190-1206 (1958)). It is also possible to employ ortho-phthalaldehyde rather than ninhydrin for post-column derivatization. An overview article on ion exchange chromatography can be found in Pickering (LC.GC (Magazine of Chromatographic Science 7(6):484-487 (1989)). It is likewise possible to carry out a pre-column derivatization, for example using ortho-phthalaldehyde or phenyl isothiocyanate, and to fractionate the resulting amino acid derivatives by reversed-phase chromatography (RP), preferably in the form of high-performance liquid chromatography (HPLC). A method of this type is described, for example, in Lindroth, et al. (Analytical Chemistry 51:1167-1174 (1979)). Detection is carried out photometrically (absorption, fluorescence). A review regarding amino acid analysis can be found inter alia in the textbook "Bioanalytik" by Lottspeich and Zorbas (Spektrum Akademischer Verlag, Heidelberg, Germany 1998).

The term DSMZ denotes the depository Deutsche Sammlung fur Mikroorganismen and Zellkulturen located in Braunschweig, Germany. The term ATCC denotes the depository American Type Culture Collection located in Manasass, Va., US. The term FERM denotes the depository National Institute of Technology and Evaluation (NITE) located in Tokyo, Japan. Two other well-known depositories are KCCM and NRRL. The term KCCM denotes the depository Korean Culture Center of Microorganisms located in Seoul, Korea. The term NRRL denotes the depository Agricultural Research Service Culture Collection located in Peoria, Ill., US.

Details regarding the biochemistry and chemical structure of polynucleotides and polypeptides as present in living things such as bacteria like *Corynebacterium* or *Escherichia*, for example, can be found inter alia in the text book "Biochemie" by Berg et al. (Spektrum Akademischer Verlag Heidelberg, Berlin, Germany, 2003; ISBN 3-8274-1303-6).

Polynucleotides consisting of deoxyribonucleotide monomers containing the nucleobases or bases resp. adenine (a), guanine (g), cytosine (c) and thymine (t) are referred to as deoxyribopolynucleotides or deoxyribonucleic acid (DNA). Polynucleotides consisting of ribonucleotide monomers containing the nucleobases or bases resp. adenine (a), guanine (g), cytosine (c) and uracil (u) are referred to as ribo-polynucleotides or ribonucleic acid (RNA). The monomers in said polynucleotides are covalently linked to one another by a 3',5'-phosphodiester bond. By convention single strand polynucleotides are written from 5'- to 3'-direction. Accordingly a polynucleotide has a 5'-end and 3'-end. The order of the nucleotide monomers in the polynucleotide is commonly referred to as nucleotide sequence. Accordingly a polynucleotide is characterized by its nucleotide sequence. For the purpose of this invention deoxyribopolynucleotides are preferred. In bacteria, for example *Corynebacterium* or *Escherichia*, the DNA is typically present in double stranded form. Accordingly the length of a DNA molecule is typically given in base pairs (bp). The nucleotide sequence coding for a specific polypeptide is called coding sequence (cds).

A gene from a chemical point of view is a polynucleotide, preferably a deoxyribopolynucleotide.

The term gene refers to a polynucleotide comprising a nucleotide sequence coding for a specific polypeptide (coding sequence) and the adjoining stop codon. In a broader sense the term includes regulatory sequences preceding and following the coding sequence. The preceding sequence is located at the 5'-end of the coding sequence and is also referred to as upstream sequence. A promotor is an example of a regulatory sequence located 5' to the coding sequence. The sequence following the coding sequence is located at its 3'-end and also referred to as downstream sequence. A transcriptional terminator is an example of a regulatory sequence located 3' to the coding sequence.

Polypeptides consist of L-amino acid monomers joined by peptide bonds. For abbreviation of L-amino acids the one letter code and three letter code of IUPAC (International Union of Pure and Applied Chemistry) is used. Due to the nature of polypeptide biosynthesis polypeptides have an amino terminal end and a carboxyl terminal end also referred to as N-terminal end and C-terminal end. The order of the L-amino acids or L-amino acid residues resp. in the polypeptide is commonly referred to as amino acid sequence. Polypeptides are also referred to as proteins.

Further it is known in the art that the start codon or initiation codon resp. gtg of a coding sequence as well as atg encodes the amino acid methionine.

Experimental Section

A) Materials and Methods

The molecular biology kits, primers and chemicals used and some details of the methods applied are briefly described herewith.

1. Chemicals
   a. Kanamycin solution from *Streptomyces kanamyceticus* was purchased from Sigma Aldrich (St. Louis, USA, Cat. no. K0254).
   b. Nalidixic acid sodium salt was purchased from Sigma Aldrich (St. Louis, USA, Cat. no. N4382).
   c. If not stated otherwise, all other chemicals were purchased analytically pure from Merck (Darmstadt, Germany), Sigma Aldrich (St. Louis, USA) or Carl-Roth (Karlsruhe, Germany).

2. Cultivation
   If not stated otherwise, all cultivation/incubation procedures were performed as described in the following:
   a. LB broth (MILLER) from Merck (Darmstadt, Germany; Cat. no. 110285) was used to cultivate *E. coli* strains in liquid medium. The liquid cultures (10 ml liquid medium per 100 ml Erlenmeyer flask with 3 baffles) were incubated in the Infors HT Multitron standard incubator shaker from Infors GmbH (Bottmingen, Switzerland) at 37° C. and 200 rpm.
   b. LB agar (MILLER) from Merck (Darmstadt, Germany Cat. no. 110283) was used for cultivation of *E. coli* strains on agar plates. The agar plates were incubated at 37° C. in an INCU-Line® mini incubator from VWR (Radnor, USA).
   c. Brain heart infusion broth (BHI) from Merck (Darmstadt, Germany; Cat. no. 110493) was used to cultivate C. glutamicum strains in liquid medium. The liquid cultures (10 ml liquid medium per 100 ml Erlenmeyer flask with 3 baffles) were incubated in the Infors HT Multitron standard incubator shaker from Infors GmbH (Bottmingen, Switzerland) at 33° C. and 200 rpm.

d. Brain heart agar (BHI-agar) from Merck (Darmstadt, Germany; Cat. no. 113825) was used for cultivation of C. glutamicum strains on agar plates. The agar plates were incubated at 33° C. in an incubator from Heraeus Instruments with Kelvitron® temperature controller (Hanau, Germany).

3. Determining Optical Density
a. The optical density of bacterial suspensions in shake flask cultures was determined at 600 nm (OD600) using the BioPhotometer from Eppendorf AG (Hamburg, Germany).
b. The optical density of bacterial suspensions produced in the Wouter Duetz (WDS) micro fermentation system (24-Well Plates) was determined at 660 nm (OD660) with the GENios™ plate reader from Tecan Group AG (Männedorf, Switzerland).

4. Centrifugation
a. Benchtop centrifuge for reaction tubes with a volume up to 2 ml Bacterial suspensions with a maximum volume of 2 ml were caused to sediment using 1 ml or 2 ml reaction tubes (e.g. Eppendorf Tubes® 3810X) using an Eppendorf 5417 R centrifuge (5 min. at 13.000 rpm).
b. Benchtop centrifuge for tubes with a volume up to 50 ml Bacterial suspensions with a maximum volume of 50 ml were caused to sediment using 15 ml or 50 ml centrifuge tubes (e.g. Falcon™ 50 ml Conical Centrifuge Tubes) using an Eppendorf 5810 R centrifuge for 10 min. at 4.000 rpm.

5. DNA Isolation
a. Plasmid DNA was isolated from E. coli cells using the QIAprep Spin Miniprep Kit from Qiagen (Hilden, Germany, Cat. No. 27106).
b. Total DNA from C. glutamicum was isolated using the method of Eikmanns et al. (Microbiology 140, 1817-1828, 1994).

6. Polymerase chain reaction (PCR)
PCR with a proof reading (high fidelity) polymerase was used to amplify a desired segment of DNA before Gibson Assembly or Sanger sequencing. Non-proof reading polymerase Kits were used for determining the presence or absence of a desired DNA fragment directly from E. coli or C. glutamicum colonies.

a. The Phusion® High-Fidelity DNA Polymerase Kit (Phusion Kit) from New England BioLabs Inc. (Ipswich, USA, Cat. No. M0530) was used for template-correct amplification of selected DNA regions according to the instructions of the manufacturer (see table 4).

TABLE 4

Thermocycling conditions for PCR with Phusion ® High-Fidelity DNA Polymerase Kit from NEB Inc.
PCR-program

| Step | Time [min.:sec.] | T [° C.] | Description |
|---|---|---|---|
| 1 | 00:30 | 98 | Initial denaturation step |
| 2 | 00:05 | 98 | Denaturation step |
| 3 | 00:30 | 60 | Annealing step |
| 4 | 00:xx | 72 | Elongation step 1 min. per kb DNA Repeat step 2 to 4: 35 x |
| 5 | 05:00 | 72 | Final Elongation step |
| 6 | Hold | 4 | Cooling step | b. Taq PCR Core Kit (Taq Kit) from Qiagen (Hilden, Germany; Cat. No. 201203) was used to amplify a desired segment of DNA in order to confirm its presence. The kit was used according to the instructions of the manufacturer (see table 5).

TABLE 5

Thermocycling conditions for PCR with Taq PCR Core Kit (Taq Kit) from Qiagen.
PCR-program

| Step | Time [min.:sec.] | T [° C.] | Description |
|---|---|---|---|
| 1 | 05:00 | 94 | Initial denaturation step |
| 2 | 00:30 | 94 | Denaturation step |
| 3 | 00:30 | 52 | Annealing step |
| 4 | 01:20 | 72 | Elongation step 1 min. per kb DNA Repeat step 2 to 4: 35 x |
| 5 | 04:00 | 72 | Final Elongation step |
| 6 | Hold | 4 | Cooling step | c. SapphireAmp® Fast PCR Master Mix (Sapphire Mix) from Takara Bio Inc (Takara Bio Europe S.A.S.; Saint-Germain-en-Laye, France; Cat. No. RR350A/B) was used as an alternative to confirm the presence of a desired segment of DNA in cells taken from E. coli or C. glutamicum colonies according to the instructions of the manufacturer (see table 6).

TABLE 6

Thermocycling conditions for PCR with SapphireAmp ® Fast PCR Master Mix (Sapphire Mix) from Takara Bio Inc.
PCR-program

| Step | Time [min.:sec.] | T [° C.] | Description |
|---|---|---|---|
| 1 | 01:00 | 94 | Initial denaturation step |
| 2 | 00:05 | 98 | Denaturation step |
| 3 | 00:05 | 55 | Annealing step |
| 4 | 00:05 | 72 | Elongation step Repeat step 2 to 4: 30 x |
| 5 | 04:00 | 72 | Final Elongation step |
| 6 | Hold | 4 | Cooling step | d. Primer
The oligonucleotides used were synthesized by Eurofins Genomics GmbH (Ebersberg, Germany) using the phosphoramidite method described by McBride and Caruthers (Tetrahedron Lett. 24, 245-248, 1983).

e. Template
As PCR template either a suitably diluted solution of isolated plasmid DNA or of isolated total DNA from a C. glutamicum liquid culture or the total DNA contained in a colony was used (colony PCR). For said colony PCR the template was prepared by taking cell material with a toothpick from a colony on an agar plate and placing the cell material directly into the PCR reaction tube. The cell material was heated for 10 sec. with 800 W in a microwave oven type Mikrowave & Grill from SEVERIN Elektrogerate GmbH (Sundern, Germany) and then the PCR reagents were added to the template in the PCR reaction tube.

f. PCR Cycler

PCR experiments were carried out in PCR cyclers type Mastercycler or Mastercycler nexus gradient from Eppendorf AG (Hamburg, Germany).

7. Restriction Enzyme Digestion of DNA

The FastDigest restriction endonucleases (FD) and the associated buffer from ThermoFisher Scientific (Waltham, USA, Cat. No. FD0684) were used for restriction digestion of the plasmid DNA. The reactions were carried out according to the instructions of the manufacturer's manual.

8. Determining the Size of DNA Fragments

The size of DNA fragments was determined by automatic capillary electrophoresis using the QIAxcel from Qiagen (Hilden, Germany).

9. Purification of PCR Amplificates and Restriction DNA Fragments

PCR amplificates and restriction DNA fragments were cleaned up using the QIAquick PCR Purification Kit from Qiagen (Hilden, Germany; Cat. No. 28106), according to the manufacturer's instructions.

10. Determining DNA Concentration

DNA concentration was measured using the NanoDrop Spectrophotometer ND-1000 from PEQLAB Biotechnologie GmbH, since 2015 VWR brand (Erlangen, Germany).

11. Gibson Assembly

Expression vectors and vectors allowing integration of the desired mutation into the chromosome were made using the method of Gibson et al. (Science 319, 1215-20, 2008). The Gibson Assembly Kit from New England BioLabs Inc. (Ipswich, USA; Cat. No. E2611) was used for this purpose. The reaction mix, containing the restricted vector and at least one DNA insert, was incubated at 50° C. for 60 min. 0.5 µl of the Assembly mixture was used for a transformation experiment.

12. Chemical Transformation of E. coli a. Chemically competent E. coli Stellar™ cells were purchased from Clontech Laboratories Inc. (Mountain View, USA; Cat. No. 636763) and transformed according to the manufacturer's protocol (PT5055-2).

These cells were used as transformation hosts for reaction mixtures obtained by Gibson Assembly. The transformation batches were cultivated overnight for approximately 18 h at 37° C. and the transformants containing plasmids selected on LB agar supplemented with 50 mg/l kanamycin.

b. E. coli K-12 strain S17-1 was used as donor for conjugational transfer of plasmids based on pK18mobsacB from E. coli to C. glutamicum. Strain S17-1 is described by Simon, R. et al. (Bio/Technology 1, 784-794, 1983). It is available from the American Type Culture Collection under the access number ATCC47055.

Chemically competent E. coli S17-1 cells were made as follows: A preculture of 10 ml LB medium (10 ml liquid medium per 100 ml Erlenmeyer flask with 3 baffles) was inoculated with 100 µl bacterial suspension of strain S17-1 and the culture was incubated overnight for about 18 h at 37° C. and 250 rpm. The main culture (70 ml LB contained in a 250 ml Erlenmeyer flask with 3 baffles) was inoculated with 300 µl of the preculture and incubated up to an OD600 of 0.5-0.8 at 37° C. The culture was centrifuged for 6 min. at 4° C. and 4000 rpm and the supernatant was discarded. The cell pellet was resuspended in 20 ml sterile, ice-cold 50 mM $CaCl_2$ solution and incubated on ice for 30 min. After another centrifugation step, the pellet was resuspended in 5 ml ice-cold 50 mM $CaCl_2$ solution and the suspension incubated on ice for 30 min. The cell suspension was then adjusted to a final concentration of 20% glycerol (v/v) with 85% sterile ice-cold glycerol. The suspension was divided into 50 µl aliquots and stored at −80° C.

To transform S17-1 cells, the protocol according to Tang, et al. (Nucleic Acids Res. 22(14), 2857-2858, 1994) with a heat shock of 45 sec. was used.

13. Conjugation of C. glutamicum

The pK18mobsacB plasmid system described by Schafer et al. (Gene 145, 69-73, 1994) was used to integrate desired DNA fragments into the chromosome of C. glutamicum. A modified conjugation method of Schäfer, et al. (Journal of Bacteriology 172, 1663-1666, 1990) was used to transfer the respective plasmid into the desired C. glutamicum recipient strain.

Liquid cultures of the C. glutamicum strains were carried out in BHI medium at 33° C. The heat shock was carried out at 48.5° C. for 9 min. Transconjugants resulting from a first recombination event were selected by plating the conjugation batch on EM8 agar (Table 7), which was supplemented with 25 mg/l kanamycin and 50 mg/l nalidixic acid. The EM8 agar plates were incubated for 72 h at 33° C.

TABLE 7

Composition of the EM8 agar.

| Components | Concentration (g/l) |
| --- | --- |
| Glucose (sterile-filtered) | 23 |
| CSL (corn steep liquor) | 30 |
| Peptone from soymeal (Merck, Germany) | 40 |
| $(NH_4)_2SO_4$ | 8 |
| Urea | 3 |
| $KH_2PO_4$ | 4 |
| $MgSO_4 \cdot 7\ H_2O$ | 0.5 |
| $FeSO_4 \cdot 7\ H_2O$ | 0.01 |
| $CuSO_4 \cdot 5\ H_2O$ | 0.001 |
| $ZnSO_4 \cdot 7\ H_2O$ | 0.01 |
| Calcium pantothenate, D(+) | 0.01 |
| Thiamine | 0.001 |
| Inositol | 0.1 |
| Nicotinic acid | 0.001 |
| Biotin (sterile-filtered) | 0.005 |
| $CaCO_3$ (autoclaved separately) | 1.6 |
| Agar-Agar (Merck, Germany) | 14 |

Sterile toothpicks were used to transfer the transconjugants onto BHI agar, which was supplemented with 25 mg/l kanamycin and 50 mg/l nalidixic acid. The agar plates were incubated for 20 h at 33° C. The cultures of the respective transconjugants produced in this manner were then propagated further for 24 h at 33° C. in 10 ml BHI medium contained in 100 ml Erlenmeyer flasks with 3 baffles. To isolate clones having encountered a second recombination event an aliquot was taken from the liquid culture, suitably diluted and plated (typically 100 to 200 µl) on BHI agar which was supplemented with 10% saccharose. The agar plates were incubated for 48 h at 33° C. The colonies growing on the saccharose containing agar plates were then examined for the phenotype kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Transconjugant clones that proved to be sensitive to kanamycin and resistant to saccharose were examined for integration of the desired genetic feature into the chromosome by means of PCR.

14. Determining Nucleotide Sequences

Nucleotide sequences of DNA molecules were determined by Eurofins Genomics GmbH (Ebersberg, Germany) by cycle sequencing, using the dideoxy chain termination method of Sanger et al. (Proceedings of the National Academy of Sciences USA 74, 5463-5467, 1977), on Applied Biosystems® (Carlsbad, Calif., USA) 3730xl DNA Analyzers. Clonemanager Professional 9 software from Scientific & Educational Software (Denver, USA) was used to visualise and evaluate the sequences.

15. Glycerol Stocks of E. coli and C. glutamicum Strains

For long time storage of E. coli and C. glutamicum strains glycerol stocks were prepared. Selected E. coli clones were cultivated in 10 ml LB medium supplemented with 2 g/l glucose. Selected C. glutamicum clones were cultivated in two fold concentrated BHI medium supplemented with 2 g/l glucose. Cultures of plasmid containing E. coli strains were supplemented with 50 mg/l kanamycin. Cultures of plasmid containing C. glutamicum strains were supplemented with 25 mg/l kanamycin. The medium was contained in 100 ml Erlenmeyer flasks with 3 baffles. It was inoculated with a loop of cells taken from a colony. The culture was then incubated for about 18 h at 37° C. and 200 rpm in the case of E. coli and 33° C. and 200 rpm in the case of C. glutamicum. After said incubation period 1.2 ml 85% (v/v) sterile glycerol were added to the culture. The obtained glycerol containing cell suspension was then aliquoted in 2 ml portions and stored at −80° C.

16. Cultivation System According to Wouter Duetz

The millilitre-scale cultivation system according to Duetz (Trends Microbiol. 2007; 15(10):469-75) was used to investigate the performance of the C. glutamicum strains constructed. For this purpose, 24-deepwell microplates (24 well WDS plates) from EnzyScreen BV (Heemstede, Netherlands; Cat. no. CR1424), filled with 2.5 mL medium were used.

Precultures of the strains were done in 10 ml two fold concentrated BHI medium. The medium was contained in a 100 ml Erlenmeyer flask with 3 baffles. It was inoculated with 100 µl of a glycerol stock culture and the culture incubated for 24 h at 33° C. and 200 rpm.

After said incubation period the optical densities OD600 of the precultures were determined.

The main cultures were done by inoculating the 2.5 ml medium containing wells of the 24 Well WDS-Plate with an aliquot of the preculture to give an optical density OD600 of 0.1.

As medium for the main culture CGXII medium described by Keilhauer et al. (J. Bacteriol. 1993 September; 175(17): 5595-5603) was used. For convenience the composition of the CGXII medium is shown in table 8.

TABLE 8

Composition of Keilhauer's CGXII medium.

| Components | Concentration (g/l) |
| --- | --- |
| MOPS (3-(N-Morpholino)propanesulfonic acid) | 42 |
| $(NH_4)_2SO_4$ | 20 |
| Urea | 5 |
| $KH_2PO_4$ | 1 |
| $K_2HPO_4$ | 1 |
| $MgSO_4 \cdot 7 H_2O$ | 0.25 |
| $CaCl_2$ | 0.01 |
| $FeSO_4 \cdot 7 H_2O$ | 0.01 |
| $MnSO_4 H_2O$ | 0.01 |
| $ZnSO_4 \cdot 7 H_2O$ | 0.001 |
| $CuSO_4 \cdot 5 H_2O$ | 0.0002 |
| $NiCl_2 6 H_2O$ | 0.00002 |
| Biotin (sterile-filtered) | 0.0002 |
| Protocatechuic acid (sterile-filtered) | 0.03 |
| Carbon source (sterile-filtered) | as needed |
| adjust the pH to 7 with NaOH | |

These main cultures were incubated for approximately 45 h at 33° C. and 300 rpm in an Infors HT Multitron standard incubator shaker from Infors GmbH (Bottmingen, Switzerland) until complete consumption of glucose.

The glucose concentration in the suspension was analysed with the blood glucose-meter OneTouch Vita® from LifeScan (Johnson & Johnson Medical GmbH, Neuss, Germany).

After cultivation the culture suspensions were transferred to a deep well microplate. A part of the culture suspension was suitably diluted to measure the OD600. Another part of the culture was centrifuged and the concentration of L-amino acids, in particular L-lysine, and residual glucose were analysed in the supernatant.

17. Amino Acid Analyser

The concentration of L-amino acids, in particular L-lysine, in the culture supernatants was determined by ion exchange chromatography using a SYKAM S433 amino acid analyser from SYKAM Vertriebs GmbH (Fürstenfeldbruck, Germany). As solid phase a column with spherical, polystyrene-based cation exchanger (Peek LCA N04/Na, dimension 150×4.6 mm) from SYKAM was used. Depending on the L-amino acid the separation takes place in an isocratic run using a mixture of buffers A and B for elution or by gradient elution using said buffers. As buffer A an aqueous solution containing in 20 l 263 g trisodium citrate, 120 g citric acid, 1100 ml methanol, 100 ml 37% HCl and 2 ml octanoic acid (final pH 3.5) was used. As buffer B an aqueous solution containing in 20 l 392 g trisodium citrate, 100 g boric acid and 2 ml octanoic acid (final pH 10.2) was used. The free amino acids were colored with ninhydrin through post-column derivatization and detected photometrically at 570 nm.

B) Experimental Results

Example 1

Sequence of the cmr gene of C. glutamicum strain DM1933 and DM1797 Strain DM1933 is an L-lysine producer described by Blombach, et al., (Applied and Environmental Microbiology 75(2), 419-427, 2009). It is deposited according to the Budapest treaty at the DSMZ under accession number DSM25442.

The nucleotide sequence of the chromosome of strain DM1933 was determined by Illumina whole-genome sequencing technology (Illumina Inc., San Diego, Calif., US). See, e.g., Benjak et al. (2015) Whole-Genome Sequencing for Comparative Genomics and De Novo Genome Assembly. In: Parish T., Roberts D. (eds) Mycobacteria Protocols. Methods in Molecular Biology, Vol 1285. Humana Press, NY, US) and Bennet, S. (Pharmacogenomics 5(4), 433-438, 2004).

It was found that the nucleotide sequence of the cmr coding sequence including the nucleotide sequence upstream and downstream thereof is identical to that of ATCC13032 as shown in SEQ ID NO:7.

Strain DM1797 is an L-lysine producer described in U.S. Pat. No. 7,338,790 B2 (see column 30). It is deposited according to the Budapest treaty at the DSMZ under accession number DSM16833. DM1797 is an aminoethylcystein resistant mutant of strain ATCC13032 obtained after N'-methyl-N-nitro-nitrosoguanidine mutagenesis.

The nucleotide sequence of the cmr coding sequence of DM1797 including the nucleotide sequence upstream and downstream thereof is identical to that of ATCC13032 shown in SEQ ID NO:7.

DM1797 contains in its chromosome a variant of the aspartokinase gene encoding a feed-back resistant aspartokinase polypeptide. Said feed-back resistant aspartokinase polypeptide has the amino acid sequence of SEQ ID NO:15 of the sequence listing, wherein the amino acid L-threonine (Thr) at position 311 of the amino acid sequence is replaced by L-isoleucine (Ile). In U.S. Pat. No. 7,338,790 the abbreviation "lysC T311I" is used to indicate said exchange.

Strain DM1933 also contains said variant of the aspartokinase gene. It is abbreviated as "lysC(T311I)" by Blombach et al. (see table 1 of Blombach, et al.)

Example 2

Construction of plasmid pK18mobsacB_Dcmr

Plasmid pK18mobsacB_Dcmr was constructed to enable incorporation of a deletion, comprising the cmr coding sequence and the adjoining stop codon accompanied by the insertion of the recognition site for the restriction endonuclease EcoRV, into the chromosome of a desired *C. glutamicum* strain. The plasmid is based on the mobilizable vector pK18mobsacB described by Schäfer, et al. (Gene 145, 69-73, 1994). For the construction of pK18mobsacB_Dcmr the Gibson Assembly method was used.

For this purpose three polynucleotides or DNA molecules resp. were generated: One polynucleotide called cmr_up comprising the upstream sequence (5'-flanking sequence) and a second polynucleotide called cmr_down comprising the downstream sequence (3'-flanking sequence) of the coding sequence of cmr. The third polynucleotide was plasmid pK18mobsacB linearized by treatment with restriction endonuclease XbaI. The polynucleotides cmr_up and cmr_down were fused during the Gibson Assembly process to give the polynucleotide Dcmr, comprising the nucleotide sequence of SEQ ID NO:13, contained in pK18mobsacB_Dcmr.

Polynucleotides cmr_up and cmr_down were synthesized by PCR using total DNA isolated from a *C. glutamicum* ATCC13032 culture as template. For PCR the Phusion Kit was used with an elongation step (see table 4, step 4) of 15 sec. For amplification of the upstream sequence (polynucleotide cmr_up) the primers 1f-Dcmr and 1r-Dcmr and for amplification of the downstream sequence (polynucleotide cmr_down) the primers 2f-Dcmr and 2r-Dcmr were used (table 9). The primers are also shown in SEQ ID NO:16 to SEQ ID NO:19 of the sequence listing.

TABLE 9

List of primers used and size of amplificates during Phusion Kit PCR.

| synthesis of amplificate | name | sequence | size [bp] |
|---|---|---|---|
| cmr_up | 1f-Dcmr | AGCTCGGTACCCGGGGATCCTGTGCCACA AAATTTAGCCTGTC | 847 |
|  | 1r-Dcmr | CAAACAACGGTCTAGAGCACGATATCGG GGTGTCTCCTAAAGATGG |  |
| cmr_down | 2f-Dcmr | CCATCTTTAGGAGACACCCCGATATCGTG CTCTAGACCGTTGTTTG | 846 |
|  | 2r-Dcmr | TGCATGCCTGCAGGTCGACTCTTGCCGAA GGCTACTACCTG |  |

The nucleotide sequence of the amplificate cmr_up is shown in SEQ ID NO:20. The nucleotide sequence of the amplificate $cmr_{13}$ down is shown in SEQ ID NO:21.

Amplificate cmr_up contains a sequence of 800 nucleotides of the upstream region of the cmr coding sequence of ATCC13032. At its 5'-end it is equipped with a sequence overlapping with a sequence of pK18mobsacB cut with XbaI. At its 3'-end it is equipped with a sequence overlapping with a sequence of the amplificate cmr_down. Said sequence at the 3'-end contains the recognition site for the restriction endonuclease EcoRV.

Amplificate cmr_down contains a sequence of 800 nucleotides of the downstream region of the cmr coding sequence of ATCC13032. At its 5'-end it is equipped with a sequence overlapping with a sequence of the amplificate cmr_up. Said sequence at the 5'-end contains the recognition site for the restriction endonuclease EcoRV. At its 3'-end it is equipped with a sequence overlapping with a sequence of pK18mobsacB cut with XbaI. Said overlapping sequences are required for the Gibson assembly technique.

Plasmid pK18mobsacB was linearized with the restriction endonuclease XbaI. The digestion mixture was controlled by capillary electrophoresis, purified and the DNA concentration quantified.

To assemble the plasmid pK18mobsacB_Dcmr the three polynucleotides i.e. the vector pK18mobsacB cut with XbaI, the amplificate cmr_up and the amplificate cmr_down were mixed using the Gibson Assembly Kit. The assembly mixture thus obtained was used to transform chemically competent *E. coli* Stellar™ cells.

Fifty kanamycin resistant transformants were analyzed by colony PCR using the Taq Kit and the primers pCV22_1.p and pCV22_2.p according to the protocol shown in table 5. The primers are shown in table 10 and under SEQ ID NO:22 and SEQ ID NO:23 of the sequence listing. The size of the amplificates was controlled by capillary electrophoresis.

TABLE 10

List of primers used for colony PCR and size of amplificate during Taq Kit PCR.

| indication for the presence of | name | sequence | size [bp] |
|---|---|---|---|
| Dcmr | pCV22_1.p | AGGTTTCCCGACTGGAAAGC | 1893 |
|  | pCV22_2.p | TGCAAGGCGATTAAGTTGGG |  |

One of the transformants thus characterized containing a plasmid of the desired size was called Stellar/pK18mobsacB_Dcmr and saved as a glycerol stock.

DNA of the plasmid pK18mobsacB_Dcmr was isolated from said transformant and the polynucleotide Dcmr created within pK18mobsacB during the Gibson assembly was analyzed by Sanger sequencing using the primers pVW_1.p and M13For shown in table 11. Said primers are also shown under SEQ ID NO:24 and SEQ ID NO:25 of the sequence listing.

TABLE 11

List of primers used for Sanger sequencing.

| detection of | name | sequence |
|---|---|---|
| Dcmr | pVW_1.p | GTGAGCGGATAACAATTTCACAC |
|  | M13For | GTAAAACGACGGCCAG |

The analysis of the nucleotide sequence thus obtained showed that the polynucleotide Dcmr contained in pK18mobsacB_Dcmr had the nucleotide sequence presented in SEQ ID NO:13.

Example 3

Construction of Strain DM1933_Δcmr::EcoRV

The pK18mobsacB_Dcmr plasmid was used to incorporate the deletion of the complete cmr coding sequence and the adjoining stop codon accompanied by the insertion of the recognition site for the restriction enzyme EcoRV into the chromosome of the L-lysine producer DM1933.

Said deletion of the complete cmr coding sequence and the adjoining stop codon accompanied by the insertion of the recognition site for the restriction enzyme EcoRV is abbreviated as Δcmr::EcoRV or deltacmr::EcoRV when appropriate.

Chemically competent cells of E. coli strain S17-1 were transformed with plasmid DNA of pK18mobsacB_Dcmr obtained in example 2. The modified conjugation method from Schäfer et al. (Journal of Bacteriology 172, 1663-1666, 1990) as described in materials and methods was used for conjugal transfer into the strain DM1933 and for selection of transconjugant clones by virtue of their saccharose resistance and kanamycin sensitivity phenotype.

Transconjugant clones were analyzed by colony PCR using the primers NCgl2679_fw and NCgl2679_rev listed in table 12, followed by size determination of the amplificates by capillary electrophoresis. The primers are also shown in SEQ ID NO:26 and SEQ ID NO:27 of the sequence listing. For PCR the Sapphire Mix (see table 6) was used.

TABLE 12

List of primers used for colony PCR and size of amplificate during Sapphire Mix PCR.

| amplification/ detection of | name | sequence | size [bp] |
|---|---|---|---|
| Δcmr::EcoRV | NCgl2679_fw | CTGGAGATGCGAGTGGGTTG | 309 |
|  | NCgl2679_rev | TGCTGCTTCTTTGGGTGTAG |  |

One of the transconjugant clones thus characterized was called DM1933_Δcmr::EcoRV. A glycerol stock culture of the transconjugant clone was prepared and used as starting material for further investigations.

The nucleotide sequence of the chromosomal region of strain DM1933_Δcmr::EcoRV containing the mutated nucleotide sequence, i.e. lack (deletion) of the cmr coding sequence and the adjoining stop codon accompanied by insertion of the recognition site for the restriction endonuclease EcoRV, was analyzed by Sanger sequencing.

For this purpose a PCR amplificate was produced spanning the site of mutation. A colony PCR was done using the primers NCgl2679_fwd1 and NCgl2681_rev1 (see table 13) and the Phusion Kit (see table 4) with an elongation time of 45 sec. (step 4 of table 4). The amplificate obtained was then sequenced using the primers NCgl2679_fwd2 and NCgl2681_rev2 (see table 13). The nucleotide sequences of the primers used in this context are also shown in SEQ ID NO:28 to 31.

TABLE 13

List of primers used for colony PCR and Sanger sequencing.

| amplification/<br>detection of | name | sequence | size<br>[bp] |
|---|---|---|---|
| Δcmr::EcoRV | NCgl2679_fwd1<br>NCgl2681_rev1 | TAGCCTGTCCTGGGTGTAAC<br>CGTGCGGGCACATCATGTTG | 1525 |
| Δcmr::EcoRV | NCgl2679_fwd2 | TCGAGATCGTGGGCAGGTTC | |
| Δcmr::EcoRV | NCgl2681_rev2 | CGTGGAAGCTCCCATGTCAG | |

The nucleotide sequence obtained is shown in SEQ ID NO:32. It contains the nucleotide sequences identified in table 2 and table 3. The result showed that strain DM1933_Δcmr::EcoRV contained the desired mutation, or the desired mutated nucleotide sequence resp., in its chromosome. Thus the cmr gene of strain DM1933 was replaced by the Δcmr::EcoRV mutation.

Example 4

L-lysine Production by Strain DM1933_Δcmr::EcoRV

Strains DM1933 (reference) and DM1933_Δcmr::EcoRV were analyzed for their ability to produce L-lysine from glucose by batch cultivation using the cultivation system according to Wouter Duetz.

As medium CGXII containing 20 g/l glucose as carbon source was used. The cultures were incubated for 45 h until complete consumption of glucose as confirmed by glucose analysis using blood glucose-meter and the concentrations of L-lysine and optical density OD660 were determined. The result of the experiment is presented in table 14.

TABLE 14

L-lysine production by strain DM1933_Δcmr::EcoRV.

| strain | L-lysine[1] (g/l) | OD660 |
|---|---|---|
| DM1933 | 6.3 | 5.1 |
| DM1933_Δcmr::EcoRV | 6.9 | 4.9 |

[1] as L-lysine × HCl

The experiment shows that L-lysine production was increased in strain DM1933Δcmr::EcoRV as compared to the parent strain.

Example 5

Construction of Strains ATCC13032_Δcmr::EcoRV and DM1797_Δcmr::EcoRV

The strains ATCC13032_Δcmr::EcoRV and DM1797_Δcmr::EcoRV were constructed from ATCC13032 and DM1797 and analyzed as described in example 3.

Example 6

L-lysine Production by Strains ATCC13032_Δcmr::EcoRV and DM1797_Δcmr::EcoRV

The production test was done as described in example 4. The result is shown in table 15.

TABLE 15

L-lysine production by strains ATCC13032_Δcmr::EcoRV and DM1797_Δcmr::EcoRV

| strain | L-lysine[1] (g/l) | OD660 |
|---|---|---|
| ATCC13032 | nd[2] | 3.4 |
| ATCC13032_Δcmr::EcoRV | nd[2] | 3.2 |
| DM1797 | 3.4 | 4.5 |
| DM1797_Δcmr::EcoRV | 3.9 | 3.9 |

[1] as L-lysine × HCl
[2] not detectable

The test showed that the mutation Δcmr::EcoRV does not convert the type strain ATCC13032 into an L-lysine producer. The test further showed that in a strain carrying a feed-back resistant aspartokinase said mutation enhances formation of L-lysine.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

SEQUENCE LISTING

<160> NUMBER OF SEQ ID NOS: 32

<210> SEQ ID NO 1
<211> LENGTH: 459
<212> TYPE: PRT
<213> ORGANISM: Corynebacterium glutamicum ATCC13032
<220> FEATURE:
<221> NAME/KEY: MISC_FEATURE
<222> LOCATION: (1)..(459)
<223> OTHER INFORMATION: amino acid sequence disclosed in GenBank
      accession number U43535

<400> SEQUENCE: 1

```
Met Ser Thr Phe His Lys Val Leu Ile Asn Thr Met Ile Ser Asn Val
1               5                   10                  15

Thr Thr Gly Phe Leu Phe Phe Ala Val Val Phe Trp Met Tyr Leu Ser
            20                  25                  30

Thr Gly Asn Val Ala Leu Thr Gly Ile Val Ser Gly Ile Tyr Met Gly
        35                  40                  45

Leu Ile Ala Val Cys Ser Ile Phe Phe Gly Thr Val Asp His Asn
    50                  55                  60

Arg Lys Lys Ser Val Met Leu Phe Ser Ser Val Thr Thr Leu Val Phe
65                  70                  75                  80

Tyr Cys Leu Ser Ala Leu Val Trp Val Phe Trp Leu Glu Glu Asp Gly
                85                  90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
    130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Val
            180                 185                 190

Asp Glu Pro Glu Ile Ile Thr Gln Glu Asp Ala Gln Pro Thr Val Ser
        195                 200                 205

Asp Asp Ser Val Pro Thr Pro Thr Ser Asp Leu Ala Ile Val Ser Lys
    210                 215                 220

Gly Ile Asp Leu Lys Gly Ser Met Lys Ile Ile Leu Ser Val Pro Gly
225                 230                 235                 240

Leu Leu Ala Leu Val Leu Phe Ala Ser Phe Asn Asn Leu Ile Gly Gly
                245                 250                 255

Val Tyr Ser Ala Leu Met Asp Pro Tyr Gly Leu Glu Leu Phe Ser Pro
            260                 265                 270

Gln Leu Trp Gly Leu Leu Leu Gly Leu Thr Ser Leu Gly Phe Ile Val
        275                 280                 285

Gly Gly Ala Val Ile Ser Lys Thr Gly Leu Gly Lys Asn Pro Val Arg
    290                 295                 300

Thr Leu Leu Leu Val Asn Val Gly Val Ala Phe Val Gly Met Leu Phe
305                 310                 315                 320

Ala Ile Arg Glu Trp Trp Trp Leu Tyr Ile Leu Gly Ile Phe Ile Phe
                325                 330                 335

Met Ala Ile Thr Pro Ala Ala Glu Ala Ala Glu Gln Thr Ile Leu Gln
            340                 345                 350

Arg Val Val Pro Phe Arg Gln Gln Gly Arg Val Phe Gly Leu Ala Met
        355                 360                 365

Ala Val Glu Met Ala Ala Asn Pro Leu Ser Thr Val Ile Val Ala Ile
    370                 375                 380

Leu Ala Glu Ala Tyr Leu Ile Pro Trp Met Ala Gly Pro Gly Ala Asp
385                 390                 395                 400

Thr Ile Trp Gly Val Ile Leu Gly Glu Gly Lys Ala Arg Gly Met Ala
                405                 410                 415
```

```
Leu Met Phe Leu Ala Ser Gly Ala Ile Met Leu Val Val Leu Leu
            420                 425                 430

Ala Phe Met Ser Arg Ser Tyr Arg Lys Leu Ser Gln Tyr Tyr Ala Thr
            435                 440                 445

Thr Ser Gln Asp Ile Ala Gly Ala Ala Glu Lys
            450                 455

<210> SEQ ID NO 2
<211> LENGTH: 459
<212> TYPE: PRT
<213> ORGANISM: Corynebacterium glutamicum ATCC13032
<220> FEATURE:
<221> NAME/KEY: MISC_FEATURE
<222> LOCATION: (1)..(459)
<223> OTHER INFORMATION: amino acid sequence disclosed in GenBank
      accesion number NP_601971

<400> SEQUENCE: 2

Met Ser Thr Phe His Lys Val Leu Ile Asn Thr Met Ile Ser Asn Val
1               5                   10                  15

Thr Thr Gly Phe Leu Phe Phe Ala Val Val Phe Trp Met Tyr Leu Ser
                20                  25                  30

Thr Gly Asn Val Ala Leu Thr Gly Ile Val Ser Gly Ile Tyr Met Gly
            35                  40                  45

Leu Ile Ala Val Cys Ser Ile Phe Phe Gly Thr Val Val Asp His Asn
        50                  55                  60

Arg Lys Lys Ser Val Met Leu Phe Ser Ser Val Thr Thr Leu Val Phe
65                  70                  75                  80

Tyr Cys Leu Ser Ala Leu Val Trp Val Phe Trp Leu Glu Glu Asp Gly
                85                  90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
    130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Val
            180                 185                 190

Asp Glu Pro Glu Ile Ile Thr Gln Glu Asp Ala Gln Pro Thr Val Ser
        195                 200                 205

Asp Asp Ser Val Pro Thr Pro Thr Ser Asp Leu Ala Ile Val Ser Lys
    210                 215                 220

Gly Ile Asp Leu Lys Gly Ser Met Lys Ile Ile Leu Ser Val Pro Gly
225                 230                 235                 240

Leu Leu Ala Leu Val Leu Phe Ala Ser Phe Asn Asn Leu Ile Gly Gly
                245                 250                 255

Val Tyr Ser Ala Leu Met Asp Pro Tyr Gly Leu Glu Leu Phe Ser Pro
            260                 265                 270

Gln Leu Trp Gly Leu Leu Leu Gly Leu Thr Ser Leu Gly Phe Ile Val
        275                 280                 285

Gly Gly Ala Val Ile Ser Lys Thr Gly Leu Gly Lys Asn Pro Val Arg
    290                 295                 300
```

```
Thr Leu Leu Leu Val Asn Val Gly Val Ala Phe Val Gly Met Leu Phe
305                 310                 315                 320

Ala Ile Arg Glu Trp Trp Leu Tyr Ile Leu Gly Ile Phe Ile Phe
            325                 330                 335

Met Ala Ile Thr Pro Ala Ala Glu Ala Ala Glu Gln Thr Ile Leu Gln
            340                 345                 350

Arg Val Val Pro Phe Arg Gln Gln Gly Arg Val Phe Gly Leu Ala Met
            355                 360                 365

Ala Val Glu Met Ala Ala Asn Pro Leu Ser Thr Val Ile Val Ala Ile
370                 375                 380

Leu Ala Glu Ala Tyr Leu Ile Pro Trp Met Ala Gly Pro Gly Ala Asp
385                 390                 395                 400

Thr Ile Trp Gly Val Ile Leu Gly Glu Gly Lys Ala Arg Gly Met Ala
            405                 410                 415

Leu Met Phe Leu Ala Ser Gly Ala Ile Met Leu Val Val Val Leu Leu
            420                 425                 430

Ala Phe Met Ser Arg Ser Tyr Arg Lys Leu Ser Gln Tyr Tyr Ala Thr
            435                 440                 445

Thr Ser Gln Asp Ile Ala Gly Ala Ala Glu Lys
    450                 455

<210> SEQ ID NO 3
<211> LENGTH: 459
<212> TYPE: PRT
<213> ORGANISM: Corynebacterium glutamicum AJ1511
<220> FEATURE:
<221> NAME/KEY: MISC_FEATURE
<222> LOCATION: (1)..(459)
<223> OTHER INFORMATION: amino acid sequence disclosed in GenBank
      accession number BAV24403

<400> SEQUENCE: 3

Met Ser Thr Phe His Arg Val Leu Ile Asn Thr Met Ile Ser Asn Val
1               5                   10                  15

Thr Thr Gly Phe Leu Phe Phe Ala Val Val Phe Trp Met Tyr Leu Ser
            20                  25                  30

Thr Gly Asn Val Ala Leu Thr Gly Ile Val Ser Gly Ile Tyr Met Gly
        35                  40                  45

Leu Ile Ala Val Cys Ser Ile Phe Phe Gly Thr Val Val Asp His Asn
    50                  55                  60

Arg Lys Lys Ser Val Met Leu Phe Ser Ser Val Thr Thr Leu Val Phe
65                  70                  75                  80

Tyr Cys Leu Ser Ala Leu Val Trp Val Phe Trp Leu Glu Glu Asp Gly
                85                  90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
    130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Ile
            180                 185                 190
```

```
Asp Glu Pro Glu Ile Ile Thr Gln Glu Asp Ala Gln Pro Thr Val Ser
            195                 200                 205

Asp Asp Ser Val Pro Thr Pro Thr Ser Asp Leu Ala Ile Val Ser Lys
    210                 215                 220

Gly Ile Asp Leu Lys Gly Ser Met Lys Ile Ile Leu Ser Val Pro Gly
225                 230                 235                 240

Leu Leu Ala Leu Val Leu Phe Thr Ser Phe Asn Asn Leu Ile Gly Gly
                245                 250                 255

Val Tyr Ser Ala Leu Met Asp Pro Tyr Gly Leu Glu Leu Phe Ser Pro
            260                 265                 270

Gln Leu Trp Gly Leu Leu Leu Gly Leu Thr Ser Leu Gly Phe Ile Val
                275                 280                 285

Gly Gly Ala Val Ile Ser Lys Thr Gly Leu Gly Lys Asn Pro Val Arg
290                 295                 300

Thr Leu Leu Leu Val Asn Val Gly Val Ala Phe Val Gly Met Leu Phe
305                 310                 315                 320

Ala Ile Arg Glu Trp Trp Leu Tyr Ile Leu Gly Ile Phe Ile Phe
            325                 330                 335

Met Ala Ile Thr Pro Ala Ala Glu Ala Ala Glu Gln Thr Ile Leu Gln
                340                 345                 350

Arg Val Val Pro Phe Arg Gln Gln Gly Arg Val Phe Gly Leu Ala Met
            355                 360                 365

Ala Val Glu Met Ala Ala Asn Pro Leu Ser Thr Val Ile Val Ala Ile
            370                 375                 380

Leu Ala Glu Ala Tyr Leu Ile Pro Trp Met Ala Gly Pro Gly Ala Asp
385                 390                 395                 400

Thr Ile Trp Gly Val Ile Leu Gly Glu Gly Lys Ala Arg Gly Met Ala
                405                 410                 415

Leu Met Phe Leu Ala Ser Gly Ala Ile Met Leu Val Val Val Leu Leu
                420                 425                 430

Ala Phe Met Ser Arg Ser Tyr Arg Lys Leu Ser Gln Tyr Tyr Ala Thr
            435                 440                 445

Thr Ser Gln Asp Ile Ala Gly Ala Ala Glu Lys
        450                 455

<210> SEQ ID NO 4
<211> LENGTH: 459
<212> TYPE: PRT
<213> ORGANISM: Corynebacterium glutamicum ATCC13869
<220> FEATURE:
<221> NAME/KEY: MISC_FEATURE
<222> LOCATION: (1)..(459)
<223> OTHER INFORMATION: amino acid sequence disclosed in GenBank
      accession ANU34683

<400> SEQUENCE: 4

Met Ser Thr Phe His Arg Val Leu Ile Asn Thr Met Ile Ser Asn Val
1               5                   10                  15

Thr Thr Gly Phe Leu Phe Phe Ala Val Val Phe Trp Met Tyr Leu Ser
                20                  25                  30

Thr Gly Asn Val Ala Leu Thr Gly Ile Val Ser Gly Ile Tyr Met Gly
            35                  40                  45

Leu Ile Ala Val Cys Ser Ile Phe Phe Gly Thr Val Val Asp His Asn
        50                  55                  60

Arg Lys Lys Ser Val Met Leu Phe Ser Ser Val Thr Thr Leu Val Phe
65                  70                  75                  80
```

-continued

```
Tyr Cys Leu Ser Ala Leu Val Trp Val Phe Trp Leu Glu Glu Asp Gly
                 85                   90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
    130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Ile
            180                 185                 190

Asp Glu Pro Glu Ile Ile Thr Gln Glu Asp Ala Gln Pro Thr Val Ser
        195                 200                 205

Asp Asp Ser Val Pro Thr Pro Thr Ser Asp Leu Ala Ile Val Ser Lys
    210                 215                 220

Gly Ile Asp Leu Lys Gly Ser Met Lys Ile Ile Leu Ser Val Pro Gly
225                 230                 235                 240

Leu Leu Ala Leu Val Leu Phe Thr Ser Phe Asn Asn Leu Ile Gly Gly
                245                 250                 255

Val Tyr Ser Ala Leu Met Asp Pro Tyr Gly Leu Glu Leu Phe Ser Pro
            260                 265                 270

Gln Leu Trp Gly Leu Leu Leu Gly Leu Thr Ser Leu Gly Phe Ile Val
        275                 280                 285

Gly Gly Ala Val Ile Ser Lys Thr Gly Leu Gly Lys Asn Pro Val Arg
    290                 295                 300

Thr Leu Leu Leu Val Asn Val Gly Val Ala Phe Val Gly Met Leu Phe
305                 310                 315                 320

Ala Ile Arg Glu Trp Trp Trp Leu Tyr Ile Leu Gly Ile Phe Ile Phe
                325                 330                 335

Met Ala Ile Thr Pro Ala Ala Glu Ala Ala Gln Thr Ile Leu Gln
            340                 345                 350

Arg Val Val Pro Phe Arg Gln Gln Gly Arg Val Phe Gly Leu Ala Met
        355                 360                 365

Ala Val Glu Met Ala Ala Asn Pro Leu Ser Thr Val Ile Val Ala Ile
    370                 375                 380

Leu Ala Glu Ala Tyr Leu Ile Pro Trp Met Ala Gly Pro Gly Ala Asp
385                 390                 395                 400

Thr Ile Trp Gly Val Ile Leu Gly Glu Gly Lys Ala Arg Gly Met Ala
                405                 410                 415

Leu Met Phe Leu Ala Ser Gly Ala Ile Met Leu Val Val Val Leu Leu
            420                 425                 430

Ala Phe Met Ser Arg Ser Tyr Arg Lys Leu Ser Gln Tyr Tyr Ala Thr
        435                 440                 445

Thr Ser Gln Asp Ile Ala Gly Ala Ala Glu Lys
    450                 455
```

<210> SEQ ID NO 5
<211> LENGTH: 459
<212> TYPE: PRT
<213> ORGANISM: Corynebacterium glutamicum R
<220> FEATURE:

<221> NAME/KEY: MISC_FEATURE
<222> LOCATION: (1)..(459)
<223> OTHER INFORMATION: amino acid sequence disclosed in GenBank accession number BAF55689

<400> SEQUENCE: 5

```
Met Ser Thr Phe His Lys Val Leu Ile Asn Thr Met Ile Ser Asn Val
1               5                   10                  15

Thr Thr Gly Phe Leu Phe Phe Ala Val Val Phe Trp Met Tyr Leu Ser
            20                  25                  30

Thr Gly Asp Val Ala Leu Thr Gly Ile Val Ser Gly Ile Tyr Met Gly
        35                  40                  45

Leu Ile Ala Val Cys Ser Ile Phe Phe Gly Thr Val Val Asp His Asn
    50                  55                  60

Arg Lys Lys Ser Val Met Leu Phe Ser Ser Ile Thr Thr Leu Val Phe
65                  70                  75                  80

Tyr Cys Leu Ser Ala Leu Val Trp Val Phe Trp Leu Glu Glu Asp Gly
                85                  90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
    130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Ile
            180                 185                 190

Asp Glu Pro Glu Ile Ile Thr Gln Gly Asp Ala Gln Pro Thr Val Ser
        195                 200                 205

Asp Asp Ser Val Pro Thr Pro Thr Ser Asp Leu Ala Ile Val Ser Lys
    210                 215                 220

Gly Ile Asp Leu Lys Gly Ser Met Lys Ile Ile Leu Ser Val Pro Gly
225                 230                 235                 240

Leu Leu Ala Leu Val Leu Phe Ala Ser Phe Asn Asn Leu Ile Gly Gly
                245                 250                 255

Val Tyr Ser Ala Leu Met Asp Pro Tyr Gly Leu Glu Leu Phe Ser Pro
            260                 265                 270

Gln Leu Trp Gly Leu Leu Leu Gly Leu Thr Ser Leu Gly Phe Ile Val
        275                 280                 285

Gly Gly Ala Val Ile Ser Lys Thr Gly Leu Gly Lys Asn Pro Val Arg
    290                 295                 300

Thr Leu Leu Leu Val Asn Val Gly Val Ala Phe Val Gly Met Phe Phe
305                 310                 315                 320

Ala Ile Arg Glu Trp Trp Trp Leu Tyr Ile Leu Gly Ile Phe Ile Phe
                325                 330                 335

Met Ala Ile Thr Pro Ala Ala Glu Ala Ala Glu Gln Thr Ile Leu Gln
            340                 345                 350

Arg Val Val Pro Phe Arg Gln Gln Gly Arg Val Phe Gly Leu Ala Met
        355                 360                 365

Ala Val Glu Met Ala Ala Asn Pro Leu Ser Thr Val Ile Val Ala Ile
    370                 375                 380
```

```
Leu Ala Glu Thr Tyr Leu Ile Pro Trp Met Ala Gly Pro Gly Ala Asp
385                 390                 395                 400

Thr Ile Trp Gly Val Ile Leu Gly Glu Gly Lys Ala Arg Gly Met Ala
            405                 410                 415

Leu Met Phe Leu Ala Ser Gly Ala Ile Met Leu Val Val Val Leu Leu
        420                 425                 430

Ala Phe Met Ser Arg Ser Tyr Arg Lys Leu Ser Gln Tyr Tyr Ala Thr
    435                 440                 445

Thr Ser Gln Asp Ile Ala Gly Ala Ala Glu Lys
    450                 455
```

<210> SEQ ID NO 6
<211> LENGTH: 459
<212> TYPE: PRT
<213> ORGANISM: Corynebacterium glutamicum ATCC14067
<220> FEATURE:
<221> NAME/KEY: MISC_FEATURE
<222> LOCATION: (1)..(459)
<223> OTHER INFORMATION: amino acid sequence disclosed in GenBank
       accession number KEI24322

<400> SEQUENCE: 6

```
Met Ser Thr Phe His Lys Val Leu Ile Asn Thr Met Ile Ser Asn Val
1               5                   10                  15

Thr Thr Gly Phe Leu Phe Phe Ala Val Val Phe Trp Met Tyr Leu Ser
            20                  25                  30

Thr Gly Asn Val Ala Leu Thr Gly Ile Val Ser Gly Ile Tyr Met Gly
        35                  40                  45

Leu Ile Ala Val Cys Ser Ile Phe Phe Gly Thr Val Val Asp His Asn
50                  55                  60

Arg Lys Lys Ser Val Met Leu Phe Ser Ser Val Thr Thr Leu Val Phe
65                  70                  75                  80

Tyr Cys Leu Ser Ala Leu Val Trp Val Phe Trp Leu Glu Glu Asp Gly
                85                  90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Ile
            180                 185                 190

Asp Glu Pro Glu Ile Ile Thr Gln Gly Asp Ala Gln Pro Thr Val Ser
        195                 200                 205

Asp Asp Ser Val Pro Thr Pro Thr Ser Asp Leu Ala Ile Val Ser Lys
210                 215                 220

Gly Ile Asp Leu Lys Gly Ser Met Lys Ile Ile Leu Ser Val Pro Gly
225                 230                 235                 240

Leu Leu Ala Leu Val Leu Phe Ala Ser Phe Asn Asn Leu Ile Gly Gly
                245                 250                 255

Val Tyr Ser Ala Leu Met Asp Pro Tyr Gly Leu Glu Leu Phe Ser Pro
            260                 265                 270
```

Gln Leu Trp Gly Leu Leu Gly Leu Thr Ser Leu Gly Phe Ile Val
            275                 280                 285

Gly Gly Ala Val Ile Ser Lys Thr Gly Leu Gly Lys Asn Pro Val Arg
        290                 295                 300

Thr Leu Leu Leu Val Asn Val Gly Val Ala Phe Val Gly Met Leu Phe
305                 310                 315                 320

Ala Ile Arg Glu Trp Trp Leu Tyr Ile Leu Gly Ile Phe Ile Phe
            325                 330                 335

Met Ala Ile Thr Pro Ala Ala Glu Ala Glu Gln Thr Ile Leu Gln
            340                 345                 350

Arg Val Val Pro Phe Arg Gln Gln Gly Arg Val Phe Gly Leu Ala Met
        355                 360                 365

Ala Val Glu Met Ala Ala Asn Pro Leu Ser Thr Val Ile Val Ala Ile
        370                 375                 380

Leu Ala Glu Ala Tyr Leu Ile Pro Trp Met Ala Gly Pro Gly Ala Asp
385                 390                 395                 400

Thr Ile Trp Gly Val Ile Leu Gly Asp Gly Lys Ala Arg Gly Met Ala
            405                 410                 415

Leu Met Phe Leu Ala Ser Gly Ala Ile Met Leu Val Val Val Leu Leu
        420                 425                 430

Ala Phe Met Ser Arg Ser Tyr Arg Lys Leu Ser Gln Tyr Tyr Ala Thr
        435                 440                 445

Thr Ser Gln Asp Ile Ala Gly Ala Ala Glu Lys
    450                 455

<210> SEQ ID NO 7
<211> LENGTH: 3380
<212> TYPE: DNA
<213> ORGANISM: Corynebacterium glutamicum ATCC13032
<220> FEATURE:
<221> NAME/KEY: misc_feature
<222> LOCATION: (1)..(3380)
<223> OTHER INFORMATION: nucleotide sequence comprising locus_tag
      NCgl2680 disclosed in GenBank accession number NC_003450
<220> FEATURE:
<221> NAME/KEY: misc_feature
<222> LOCATION: (1)..(1000)
<223> OTHER INFORMATION: nucleotide sequence upstream of cds
<220> FEATURE:
<221> NAME/KEY: misc_feature
<222> LOCATION: (201)..(201)
<223> OTHER INFORMATION: nucleobase guanine
<220> FEATURE:
<221> NAME/KEY: misc_feature
<222> LOCATION: (1000)..(1000)
<223> OTHER INFORMATION: nucleobase cytosine
<220> FEATURE:
<221> NAME/KEY: CDS
<222> LOCATION: (1001)..(2377)
<220> FEATURE:
<221> NAME/KEY: misc_feature
<222> LOCATION: (2378)..(2380)
<223> OTHER INFORMATION: stop codon
<220> FEATURE:
<221> NAME/KEY: misc_feature
<222> LOCATION: (2378)..(3380)
<223> OTHER INFORMATION: nucleotide sequence downstream of cds
<220> FEATURE:
<221> NAME/KEY: misc_feature
<222> LOCATION: (2381)..(2381)
<223> OTHER INFORMATION: nucleobase guanine
<220> FEATURE:
<221> NAME/KEY: misc_feature
<222> LOCATION: (3180)..(3180)
<223> OTHER INFORMATION: nucleobase guanine

<400> SEQUENCE: 7

-continued

```
agccccgagc ctaggcgtta atgtgaccaa gcgcagcgcg ggcaaaacct aaccggtata    60
agacaccgaa acttcccta ccattcactt tggtaacccg ttggggtgcg tacgctaagt    120
attttagcgc caaccgctcg tgaggtaatc ggcttcctcg aacatgtgga ggctgtgtag   180
atcaataact aattgcacag gtgccacaaa atttagcctg tcctgggtgt aacttcccac   240
cagttccgtg accgttgcgg gcaggagaat tagatcggcg tcttctgcca catcaacaat   300
ggtgcccagc gctgagacat cgagatcgtg gcaggttcg tgccacacaa tcgaattccc    360
cagcacaatt tgtcccatga tcaccgtggc agccgcagcg cccgacagcg cccatttggt   420
tttgtgctgt tggaaaagct ccggtagctc agcgatgccg cgtggattga gtttcacaaa   480
ctgcgcatcc tggcgatgtg tgatgccctg aagcgttccg gcttcagaga caagggtgag   540
cggatcgttg atattccacc gctcaaaacg gtgcaaccaa gcgagaattt cctggttgtg   600
gggattttcg gggacggagg cgtcgataag cgtgcgcgct gcagcggccg caaagggatc   660
gcaggcgtgg tgcgcggcga ccttaatatc aagcccgagc gccaacgcga cctcacgcag   720
cgtcgacagg gtgggctcgc tggtgccatc gccgacccgc ttcagggtcg agcgcgagac   780
accggaacgc ctggagatgc gagtgggttg ctccgcggcg agagcaatca attcatcgat   840
cttcacaaca aaccatgcta atcatcacgg ttttttcgctc aggcaccggc caacgctttt   900
cgacgcgccc ctccaccttt tcagtagcgt cacgggcgcc aatcctgtat ttttagcagc   960
agtttgaggg ttttttgctcc ccatctttag gagacacccc gtg tcc acg ttt cat   1015
                                                Met Ser Thr Phe His
                                                 1               5 aaa gtt ctg atc aac acc atg atc tcc aac gtc acc act gga ttt ctg   1063
Lys Val Leu Ile Asn Thr Met Ile Ser Asn Val Thr Thr Gly Phe Leu
           10                  15                  20 ttc ttt gcc gtg gtg ttt tgg atg tat ctt tcc act ggc aac gtc gca   1111
Phe Phe Ala Val Val Phe Trp Met Tyr Leu Ser Thr Gly Asn Val Ala
               25                  30                  35 ctg acc ggc atc gtc agt gga att tac atg ggt ttg atc gcc gtt tgt   1159
Leu Thr Gly Ile Val Ser Gly Ile Tyr Met Gly Leu Ile Ala Val Cys
           40                  45                  50 tcc atc ttt ttc gga acc gtt gtt gat cac aat cgc aag aag tcc gtc   1207
Ser Ile Phe Phe Gly Thr Val Val Asp His Asn Arg Lys Lys Ser Val
 55                  60                  65 atg ctg ttt tcc agc gtc acc aca ctc gtg ttt tat tgt ctc agt gcc   1255
Met Leu Phe Ser Ser Val Thr Thr Leu Val Phe Tyr Cys Leu Ser Ala
 70                  75                  80                  85 ctg gtg tgg gtg ttt tgg ctg gag gaa gac ggc ctg agc atc gga aat   1303
Leu Val Trp Val Phe Trp Leu Glu Glu Asp Gly Leu Ser Ile Gly Asn
                 90                  95                 100 acc gcc ctg tgg gtg ttc gtt tct ttc atc ctc atc gga tca atc gtg   1351
Thr Ala Leu Trp Val Phe Val Ser Phe Ile Leu Ile Gly Ser Ile Val
                105                 110                 115 gaa cac atg cgc aac atc gca ctg tcc acc gtg gtc acg ctg ttg gtt   1399
Glu His Met Arg Asn Ile Ala Leu Ser Thr Val Val Thr Leu Leu Val
            120                 125                 130 cct gaa gct gaa cgc gac aaa gca aac ggc ctg gta gga gcc gtg caa   1447
Pro Glu Ala Glu Arg Asp Lys Ala Asn Gly Leu Val Gly Ala Val Gln
                135                 140                 145 ggt gtt gga ttt tta gtc acc agc gtc att gct ggt tcc gcc atc ggg   1495
Gly Val Gly Phe Leu Val Thr Ser Val Ile Ala Gly Ser Ala Ile Gly
150                 155                 160                 165 ttc ttg ggc atg gaa atc acc ctg tgg atc tgc ctt ggg ctc tca ctt   1543
Phe Leu Gly Met Glu Ile Thr Leu Trp Ile Cys Leu Gly Leu Ser Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 170 |     |     |     | 175 |     |     |     | 180 |     |     |     |      |
| gtc | gcg | ctg | ctg | cac | ctg | ctg | ccg | att | cgc | gtc | gac | gaa | ccg | gaa | atc | 1591 |
| Val | Ala | Leu | Leu | His | Leu | Leu | Pro | Ile | Arg | Val | Asp | Glu | Pro | Glu | Ile |      |
|     |     |     |     | 185 |     |     |     | 190 |     |     |     | 195 |     |     |     |      |
| atc | acc | caa | gaa | gac | gca | cag | cct | act | gtt | tct | gac | gat | tca | gtt | ccc | 1639 |
| Ile | Thr | Gln | Glu | Asp | Ala | Gln | Pro | Thr | Val | Ser | Asp | Asp | Ser | Val | Pro |      |
|     |     |     | 200 |     |     |     | 205 |     |     |     | 210 |     |     |     |     |      |
| aca | cct | acc | tcc | gat | ttg | gcg | atc | gtg | tcc | aaa | ggc | atc | gac | cta | aaa | 1687 |
| Thr | Pro | Thr | Ser | Asp | Leu | Ala | Ile | Val | Ser | Lys | Gly | Ile | Asp | Leu | Lys |      |
|     | 215 |     |     |     | 220 |     |     |     | 225 |     |     |     |     |     |     |      |
| gga | tca | atg | aaa | atc | atc | ctg | agt | gtt | ccg | gga | ctc | ctc | gcg | ctt | gtg | 1735 |
| Gly | Ser | Met | Lys | Ile | Ile | Leu | Ser | Val | Pro | Gly | Leu | Leu | Ala | Leu | Val |      |
| 230 |     |     |     | 235 |     |     |     | 240 |     |     |     | 245 |     |     |     |      |
| ttg | ttt | gcg | tcc | ttc | aac | aac | ctc | atc | ggc | ggc | gtg | tac | tcc | gca | ctc | 1783 |
| Leu | Phe | Ala | Ser | Phe | Asn | Asn | Leu | Ile | Gly | Gly | Val | Tyr | Ser | Ala | Leu |      |
|     |     |     | 250 |     |     |     | 255 |     |     |     | 260 |     |     |     |     |      |
| atg | gac | cct | tac | ggc | ctg | gaa | ctt | ttc | agc | cca | cag | ctg | tgg | ggg | cta | 1831 |
| Met | Asp | Pro | Tyr | Gly | Leu | Glu | Leu | Phe | Ser | Pro | Gln | Leu | Trp | Gly | Leu |      |
|     |     | 265 |     |     |     | 270 |     |     |     | 275 |     |     |     |     |     |      |
| ctg | ctt | gga | ctc | acc | agc | ctc | ggc | ttc | atc | gtt | ggt | ggt | gct | gtg | atc | 1879 |
| Leu | Leu | Gly | Leu | Thr | Ser | Leu | Gly | Phe | Ile | Val | Gly | Gly | Ala | Val | Ile |      |
|     |     |     | 280 |     |     |     | 285 |     |     |     | 290 |     |     |     |     |      |
| tcc | aaa | act | ggc | ttg | ggc | aaa | aac | cct | gtg | cgc | acc | ttg | ctg | ctg | gtt | 1927 |
| Ser | Lys | Thr | Gly | Leu | Gly | Lys | Asn | Pro | Val | Arg | Thr | Leu | Leu | Leu | Val |      |
|     | 295 |     |     |     | 300 |     |     |     | 305 |     |     |     |     |     |     |      |
| aat | gtt | ggt | gtg | gct | ttt | gtt | ggc | atg | tta | ttt | gcc | att | cgc | gaa | tgg | 1975 |
| Asn | Val | Gly | Val | Ala | Phe | Val | Gly | Met | Leu | Phe | Ala | Ile | Arg | Glu | Trp |      |
| 310 |     |     |     | 315 |     |     |     | 320 |     |     |     | 325 |     |     |     |      |
| tgg | tgg | ctc | tac | atc | ctg | ggc | att | ttc | atc | ttc | atg | gct | atc | acc | cca | 2023 |
| Trp | Trp | Leu | Tyr | Ile | Leu | Gly | Ile | Phe | Ile | Phe | Met | Ala | Ile | Thr | Pro |      |
|     |     |     | 330 |     |     |     | 335 |     |     |     | 340 |     |     |     |     |      |
| gct | gcc | gaa | gcc | gca | gaa | caa | acc | atc | ctt | caa | cga | gtc | gtc | cca | ttc | 2071 |
| Ala | Ala | Glu | Ala | Ala | Glu | Gln | Thr | Ile | Leu | Gln | Arg | Val | Val | Pro | Phe |      |
|     |     | 345 |     |     |     | 350 |     |     |     | 355 |     |     |     |     |     |      |
| cgc | caa | caa | ggc | cgc | gta | ttt | gga | cta | gcc | atg | gca | gtg | gaa | atg | gca | 2119 |
| Arg | Gln | Gln | Gly | Arg | Val | Phe | Gly | Leu | Ala | Met | Ala | Val | Glu | Met | Ala |      |
|     |     | 360 |     |     |     | 365 |     |     |     | 370 |     |     |     |     |     |      |
| gcc | aac | ccg | ctc | tcc | aca | gtg | atc | gtg | gcg | att | ttg | gcc | gaa | gcc | tac | 2167 |
| Ala | Asn | Pro | Leu | Ser | Thr | Val | Ile | Val | Ala | Ile | Leu | Ala | Glu | Ala | Tyr |      |
|     | 375 |     |     |     | 380 |     |     |     | 385 |     |     |     |     |     |     |      |
| ctc | att | cca | tgg | atg | gct | ggc | ccc | ggc | gcg | gac | acc | atc | tgg | ggc | gtg | 2215 |
| Leu | Ile | Pro | Trp | Met | Ala | Gly | Pro | Gly | Ala | Asp | Thr | Ile | Trp | Gly | Val |      |
| 390 |     |     |     | 395 |     |     |     | 400 |     |     |     | 405 |     |     |     |      |
| atc | ctc | ggc | gag | ggt | aaa | gct | cgc | ggc | atg | gca | ctg | atg | ttc | ctc | gca | 2263 |
| Ile | Leu | Gly | Glu | Gly | Lys | Ala | Arg | Gly | Met | Ala | Leu | Met | Phe | Leu | Ala |      |
|     |     |     | 410 |     |     |     | 415 |     |     |     | 420 |     |     |     |     |      |
| tca | ggt | gcc | atc | atg | ttg | gtt | gtc | gtg | ctg | ttg | gca | ttc | atg | tcg | agg | 2311 |
| Ser | Gly | Ala | Ile | Met | Leu | Val | Val | Val | Leu | Leu | Ala | Phe | Met | Ser | Arg |      |
|     |     | 425 |     |     |     | 430 |     |     |     | 435 |     |     |     |     |     |      |
| tcc | tac | cgg | aaa | ctc | agc | cag | tac | tac | gcc | acc | acc | agc | caa | gac | att | 2359 |
| Ser | Tyr | Arg | Lys | Leu | Ser | Gln | Tyr | Tyr | Ala | Thr | Thr | Ser | Gln | Asp | Ile |      |
|     |     | 440 |     |     |     | 445 |     |     |     | 450 |     |     |     |     |     |      |
| gcg | gga | gct | gct | gag | aag | taagtgctct agaccgttgt tgattggct      ||||||||||| 2407 |
| Ala | Gly | Ala | Ala | Glu | Lys |     |     |     |     |     |     |     |     |     |     |      |
|     | 455 |     |     |     |     |     |     |     |     |     |     |     |     |     |     |      | tttcttgcct gttgaacgag ggaaagaaaa acaaacagtc ctgaagctac acccaaagaa       2467 gcagcataaa ttggttccgc agggaaccca ttggcaacaa acacaagat aatcattgcg         2527 ccaacttgcc aaaccggggc cgctttttc caaaatcgaa ctgtggagaa tttattaatc         2587

```
cccccatgaca aggcaacaag gaggccgatg aaagctatgg ctaaaagaac ttgattcaga    2647
gttagcgagt aaatgaacaa tccaaaaaaa catagaagcg ataaaactct gccagtacat    2707
attcaccttg agaggctttg ggtatcggta gtcaactgat acagagggat ctattaagta    2767
catttaagag tacttcactt tgaatcgttg ttctgggatt ctctcaaccc cgggcctaaa    2827
acgtcagctc tctacaatta ggcgctctat aacgccctga aaattacccc ctgagcatgc    2887
agatcatcga gcaggatctc caaaccgtgc gacggtgaat cggggggcaat attgacagtt    2947 agcatttctg acatgggagc ttccacgtgt agcccaagtg tttctagttg ggctcgcacg    3007
tggtcagcag cgatggcatc aacgagcacc cggagggttt tgtttccgcc agcaactgcc    3067
acttcttgaa attccaagac ctcatcaaca tgatgtgccc gcacgacgtc acccagggca    3127
cagtcctggg cgacagccgg caaagtggct accaggtagt agccttcggc aagcagttct    3187
acacctacct cttctgattc cactcccgga acatcgagag gaatgcgcag ctttcctgc     3247 ttgcccacga gccgttagac cgccctggaa acgtcgagct tctggccgcc gtcggcgacg    3307
tcgacaagca caccatcgcc atcacggacg ttgcctgcca gcagttcctt agccaaagta    3367
tcaccgatgg cct                                                       3380
```

<210> SEQ ID NO 8
<211> LENGTH: 459
<212> TYPE: PRT
<213> ORGANISM: Corynebacterium glutamicum ATCC13032

<400> SEQUENCE: 8

```
Met Ser Thr Phe His Lys Val Leu Ile Asn Thr Met Ile Ser Asn Val
1               5                   10                  15

Thr Thr Gly Phe Leu Phe Phe Ala Val Val Phe Trp Met Tyr Leu Ser
            20                  25                  30

Thr Gly Asn Val Ala Leu Thr Gly Ile Val Ser Gly Ile Tyr Met Gly
        35                  40                  45

Leu Ile Ala Val Cys Ser Ile Phe Phe Gly Thr Val Val Asp His Asn
    50                  55                  60

Arg Lys Lys Ser Val Met Leu Phe Ser Ser Val Thr Thr Leu Val Phe
65                  70                  75                  80

Tyr Cys Leu Ser Ala Leu Val Trp Val Phe Trp Leu Glu Glu Asp Gly
                85                  90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
    130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Val
            180                 185                 190

Asp Glu Pro Glu Ile Ile Thr Gln Glu Asp Ala Gln Pro Thr Val Ser
        195                 200                 205

Asp Asp Ser Val Pro Thr Pro Thr Ser Asp Leu Ala Ile Val Ser Lys
    210                 215                 220
```

Gly Ile Asp Leu Lys Gly Ser Met Lys Ile Ile Leu Ser Val Pro Gly
225                 230                 235                 240

Leu Leu Ala Leu Val Leu Phe Ala Ser Phe Asn Asn Leu Ile Gly Gly
            245                 250                 255

Val Tyr Ser Ala Leu Met Asp Pro Tyr Gly Leu Glu Leu Phe Ser Pro
        260                 265                 270

Gln Leu Trp Gly Leu Leu Leu Gly Leu Thr Ser Leu Gly Phe Ile Val
    275                 280                 285

Gly Gly Ala Val Ile Ser Lys Thr Gly Leu Gly Lys Asn Pro Val Arg
    290                 295                 300

Thr Leu Leu Leu Val Asn Val Gly Val Ala Phe Val Gly Met Leu Phe
305                 310                 315                 320

Ala Ile Arg Glu Trp Trp Trp Leu Tyr Ile Leu Gly Ile Phe Ile Phe
            325                 330                 335

Met Ala Ile Thr Pro Ala Ala Glu Ala Ala Glu Gln Thr Ile Leu Gln
            340                 345                 350

Arg Val Val Pro Phe Arg Gln Gln Gly Arg Val Phe Gly Leu Ala Met
        355                 360                 365

Ala Val Glu Met Ala Ala Asn Pro Leu Ser Thr Val Ile Val Ala Ile
370                 375                 380

Leu Ala Glu Ala Tyr Leu Ile Pro Trp Met Ala Gly Pro Gly Ala Asp
385                 390                 395                 400

Thr Ile Trp Gly Val Ile Leu Gly Glu Gly Lys Ala Arg Gly Met Ala
            405                 410                 415

Leu Met Phe Leu Ala Ser Gly Ala Ile Met Leu Val Val Leu Leu
        420                 425                 430

Ala Phe Met Ser Arg Ser Tyr Arg Lys Leu Ser Gln Tyr Tyr Ala Thr
            435                 440                 445

Thr Ser Gln Asp Ile Ala Gly Ala Ala Glu Lys
450                 455

```
<210> SEQ ID NO 9
<211> LENGTH: 3380
<212> TYPE: DNA
<213> ORGANISM: Corynebacterium glutamicum ATCC13869
<220> FEATURE:
<221> NAME/KEY: misc_feature
<222> LOCATION: (1)..(3380)
<223> OTHER INFORMATION: nucleotide sequence comprising locus_tag
      BBD29_RS13550 disclosed in GenBank accession number NZ_CP016335
<220> FEATURE:
<221> NAME/KEY: misc_feature
<222> LOCATION: (1)..(1000)
<223> OTHER INFORMATION: nucleotide sequence upstream of cds
<220> FEATURE:
<221> NAME/KEY: CDS
<222> LOCATION: (1001)..(2377)
<220> FEATURE:
<221> NAME/KEY: misc_feature
<222> LOCATION: (2378)..(3380)
<223> OTHER INFORMATION: nucleotide sequence downstream cds
<220> FEATURE:
<221> NAME/KEY: misc_feature
<222> LOCATION: (2378)..(2380)
<223> OTHER INFORMATION: stop codon

<400> SEQUENCE: 9
agccccgagc ctaggcgtta atgtgaccaa gcgcagcgcg gacataacct aaccagcata      60
agacaccgaa acttccccta ccattcacat tggtaatccg ttggggtgcg tacgctaagt     120
attttaacgc caaccgctcg tgaggtaatc ggcttcctca acatgtggaa ggctgtgcag     180
```

| | |
|---|---|
| atcaataact aattgcacgg gtgccacaaa atttaacctg tcctgggtgt aacttcccac | 240 |
| caattccgtg gccgttgcgg gcatgagaat gagatcggcg tcttctgcca catcaacaat | 300 |
| ggtgcccagc gctgagacat cgagatcgtg ggcaggttcg tgccacacaa tcgaattccc | 360 |
| cagcacaatt tgtcccatga tcaccgtggc agccgcagcg cccgcagcg cccatttggt | 420 |
| tttgtgctgt tggaaaagct ccggtagctc agcgatgccg cgtggattga gtttcacaaa | 480 |
| ctgcgcatcc tggcgatgtg tgatgccctg aagcgttccg gcctcagaga caagggtgag | 540 |
| cggatcgttg atattccacc gctcaaaacg gtgcaaccaa gcgagaatgt cctggttgtg | 600 |
| gggattttcg gggacggagg cgtcgataag cgtgcgcgct gcagcggccg caaagggatc | 660 |
| gcaggcgtgg tgcgcggcga ccttaatatc aagcccgagc gccaacgcga cctcacgcag | 720 |
| cgtcgacagg gtgggctcgc tggtgccatc gccgacccgc ttcagggtcg agcgcgagac | 780 |
| accggaacgc ctggagatgc gagtgggttg ctccgcggcg agagcaatca attcatcgat | 840 |
| cttcacaaca aaccatgcta atcatcacgg ttttcgctc aggcaccggc caacgctttt | 900 |
| cgacgcaccc ctccacctttt tcagtagcgt cacgggcgcc aatcctgtat ttttagcagc | 960 |

| | | | | | | | | | | | | |
|---|---|---|---|---|---|---|---|---|---|---|---|---|
| agtttgaggg ttttgctcc ccatctttag gagacacccc | gtg Met 1 | tcc Ser | acg Thr | ttt Phe | cat His 5 | | | | | | | 1015 |
| aga Arg | gtt Val | ctg Leu | atc Ile | aac Asn 10 | acc Thr | atg Met | atc Ile | tcc Ser | aac Asn 15 | gtc Val | acc Thr | act Thr | gga Gly | ttt Phe | ctg Leu 20 | 1063 |
| ttc Phe | ttt Phe | gcc Ala | gtg Val 25 | gtg Val | ttt Phe | tgg Trp | atg Met | tat Tyr 30 | ctt Leu | tcc Ser | acc Thr | ggc Gly | aac Asn 35 | gtc Val | gca Ala | 1111 |
| ctg Leu | acc Thr | ggc Gly 40 | atc Ile | gtc Val | agt Ser | gga Gly | att Ile 45 | tac Tyr | atg Met | ggt Gly | ttg Leu | atc Ile 50 | gcc Ala | gtt Val | tgt Cys | 1159 |
| tcc Ser | atc Ile 55 | ttt Phe | ttc Phe | gga Gly | acc Thr | gtt Val 60 | gtt Val | gat Asp | cac His | aac Asn | cgc Arg 65 | aag Lys | aaa Lys | tcc Ser | gtc Val | 1207 |
| atg Met 70 | ctg Leu | ttt Phe | tcc Ser | agc Ser | gtc Val 75 | acc Thr | aca Thr | ctc Leu | gtg Val | ttt Phe 80 | tat Tyr | tgc Cys | ctc Leu | agc Ser | gca Ala 85 | 1255 |
| ctg Leu | gtg Val | tgg Trp | gtg Val | ttt Phe 90 | tgg Trp | ctg Leu | gag Glu | gaa Glu | gac Asp 95 | ggc Gly | ctg Leu | agc Ser | atc Ile | gga Gly 100 | aat Asn | 1303 |
| acc Thr | gca Ala | ctg Leu | tgg Trp 105 | gtg Val | ttc Phe | gtt Val | tct Ser | ttc Phe 110 | atc Ile | ctc Leu | atc Ile | gga Gly | tca Ser 115 | atc Ile | gtg Val | 1351 |
| gaa Glu | cac His | atg Met | cgc Arg 120 | aac Asn | atc Ile | gca Ala | ctg Leu | tcc Ser 125 | acc Thr | gtg Val | gtc Val | acg Thr | ctg Leu 130 | ttg Leu | gtt Val | 1399 |
| cct Pro | gaa Glu 135 | gct Ala | gaa Glu | cgt Arg | gac Asp | aaa Lys 140 | gca Ala | aac Asn | ggc Gly | ctg Leu | gta Val 145 | gga Gly | gcc Ala | gtg Val | caa Gln | 1447 |
| ggt Gly 150 | gtt Val | gga Gly | ttt Phe | tta Leu | gtc Val 155 | acc Thr | agc Ser | gtc Val | att Ile | gct Ala 160 | ggt Gly | tcc Ser | gcc Ala | atc Ile | ggg Gly 165 | 1495 |
| ttc Phe | ttg Leu | ggc Gly | atg Met | gaa Glu 170 | atc Ile | acc Thr | ctg Leu | tgg Trp | atc Ile 175 | tgc Cys | ctt Leu | ggg Gly | ctc Leu | tca Ser 180 | ctc Leu | 1543 |
| gtt Val | gcg Ala | ctg Leu | ctg Leu 185 | cat His | ctg Leu | ctg Leu | ccg Pro | att Ile 190 | cgc Arg | atc Ile | gac Asp | gaa Glu | ccg Pro 195 | gaa Glu | atc Ile | 1591 |
| atc Ile | acc Thr | caa Gln | gaa Glu | gac Asp | gca Ala | cag Gln | cct Pro | act Thr | gtt Val | tct Ser | gac Asp | gat Asp | tca Ser | gtt Val | ccc Pro | 1639 |

```
Ile Thr Gln Glu Asp Ala Gln Pro Thr Val Ser Asp Ser Val Pro
        200                 205                 210 aca cct acc tcc gat ttg gcg atc gtg tcc aaa ggc att gac ctt aaa    1687
Thr Pro Thr Ser Asp Leu Ala Ile Val Ser Lys Gly Ile Asp Leu Lys
215                 220                 225 gga tca atg aaa atc atc ctg agt gtt ccg gga ctg ctc gcg ctg gtg    1735
Gly Ser Met Lys Ile Ile Leu Ser Val Pro Gly Leu Leu Ala Leu Val
230                 235                 240                 245 ttg ttt acg tcc ttc aac aac ctc atc ggc ggc gtg tac tcc gca ctc    1783
Leu Phe Thr Ser Phe Asn Asn Leu Ile Gly Gly Val Tyr Ser Ala Leu
                250                 255                 260 atg gac cct tac ggc ctg gaa ctt ttc agc cca cag ctg tgg ggg cta    1831
Met Asp Pro Tyr Gly Leu Glu Leu Phe Ser Pro Gln Leu Trp Gly Leu
            265                 270                 275 ctt ctt gga ctc acc agc ctc ggc ttc atc gtt ggt ggt gct gtg atc    1879
Leu Leu Gly Leu Thr Ser Leu Gly Phe Ile Val Gly Gly Ala Val Ile
        280                 285                 290 tcc aaa act ggc ttg ggc aaa aac cct gtg cgc acc ttg ttg ctg gtt    1927
Ser Lys Thr Gly Leu Gly Lys Asn Pro Val Arg Thr Leu Leu Leu Val
295                 300                 305 aat gtt ggc gtg gct ttt gtt ggc atg tta ttt gcc atc cgc gaa tgg    1975
Asn Val Gly Val Ala Phe Val Gly Met Leu Phe Ala Ile Arg Glu Trp
310                 315                 320                 325 tgg tgg ctc tac atc ctg gga att ttc atc ttc atg gct atc acg cca    2023
Trp Trp Leu Tyr Ile Leu Gly Ile Phe Ile Phe Met Ala Ile Thr Pro
                330                 335                 340 gct gcc gaa gcc gcc gaa caa acc atc ctt caa cga gtc gtc cca ttc    2071
Ala Ala Glu Ala Ala Glu Gln Thr Ile Leu Gln Arg Val Val Pro Phe
            345                 350                 355 cgc caa caa ggc cgc gta ttt gga tta gcc atg gcg gta gaa atg gca    2119
Arg Gln Gln Gly Arg Val Phe Gly Leu Ala Met Ala Val Glu Met Ala
        360                 365                 370 gcc aac ccg ctc tcc aca gtt atc gtg gcg att ttg gcc gaa gcc tac    2167
Ala Asn Pro Leu Ser Thr Val Ile Val Ala Ile Leu Ala Glu Ala Tyr
375                 380                 385 ctc atc ccg tgg atg gca ggc ccc ggc gcg gac acc atc tgg ggc gtc    2215
Leu Ile Pro Trp Met Ala Gly Pro Gly Ala Asp Thr Ile Trp Gly Val
390                 395                 400                 405 att ctc ggc gag ggt aaa gct cgc ggc atg gca ctg atg ttc ctc gca    2263
Ile Leu Gly Glu Gly Lys Ala Arg Gly Met Ala Leu Met Phe Leu Ala
                410                 415                 420 tca ggt gcc atc atg ttg gtt gtc gtg ctg ttg gca ttc atg tcg agg    2311
Ser Gly Ala Ile Met Leu Val Val Val Leu Leu Ala Phe Met Ser Arg
            425                 430                 435 tcc tac cgg aaa ctc agc cag tac tac gcc acc acc agc caa gac att    2359
Ser Tyr Arg Lys Leu Ser Gln Tyr Tyr Ala Thr Thr Ser Gln Asp Ile
        440                 445                 450 gcg gga gct gct gag aag taagtgtctct agaccgttgt tgattggct           2407
Ala Gly Ala Ala Glu Lys
    455 tttcttgcct gttgaacgag ggaaagaaaa acaaacagtc ctgaagctac acccaaagaa  2467 gcagcataaa ttggttctgc agggaaccca ttggcaacaa aacacaagat aatcattgcg  2527 ccaacttgcc aaaccggggc ccgcttttt caaaatcgaa ctgtggagaa tttattaatc   2587 ccccatgaca aggcaacaag gaggccgatg agagctatgg ctaaaagaac ttgattcaga  2647 gttagcgagt aaatgaacaa tccaaaaaac atagaagcga taaaactctg ccagtacata  2707 ttcaccttga gaggctttgg gtatcggtag tcaactgata cagagggatc tattaagtac  2767
```

```
atttaagagt acttcacttt gaatcgttgt tcggggattc tctcaacccc gggcctaaaa    2827
cgtcagctct ctacaattag gcgctctata acgccctgaa aattacccce tgagcatgca    2887 gatcatcgag caggatctcc aaaccgtgcg acggtgaatc gggggcaata ttgacagtta    2947
gcatttctga catgggagct tccacgtata gcccaagtgt ttctagttgg gctcgcacgt    3007
ggtcagcagc gatggcatca acgagcaccc ggagggtttg gtttccgcca gcaactgcca    3067
cttcttgaaa ttccaagacc tcatcaacat gatgtgcccg cacgacgtca cccagggcac    3127
agtcctgggc gacagccggc aaagtggcta ccaggtagta gccttcggca agcagttcta    3187
cacctacctc ttctgattcc actcccggaa catcgagagg aatgcgcagc ttttcctgct    3247
tgcccacgag ccgttagacc gccctggaaa cgtcgagctt ctggccgccg tcggcgacgt    3307
cgacaagcac accatcgcca tcacggacgt tgcctgccag cagttcctta gccaaagtat    3367
caccgatggc ctg                                                       3380
```

<210> SEQ ID NO 10
<211> LENGTH: 459
<212> TYPE: PRT
<213> ORGANISM: Corynebacterium glutamicum ATCC13869

<400> SEQUENCE: 10

```
Met Ser Thr Phe His Arg Val Leu Ile Asn Thr Met Ile Ser Asn Val
1               5                   10                  15

Thr Thr Gly Phe Leu Phe Ala Val Val Phe Trp Met Tyr Leu Ser
            20                  25                  30

Thr Gly Asn Val Ala Leu Thr Gly Ile Val Ser Gly Ile Tyr Met Gly
        35                  40                  45

Leu Ile Ala Val Cys Ser Ile Phe Phe Gly Thr Val Val Asp His Asn
    50                  55                  60

Arg Lys Lys Ser Val Met Leu Phe Ser Ser Val Thr Thr Leu Val Phe
65                  70                  75                  80

Tyr Cys Leu Ser Ala Leu Val Trp Val Phe Trp Leu Glu Glu Asp Gly
                85                  90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
    130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Ile
            180                 185                 190

Asp Glu Pro Glu Ile Ile Thr Gln Glu Asp Ala Gln Pro Thr Val Ser
        195                 200                 205

Asp Asp Ser Val Pro Thr Pro Thr Ser Asp Leu Ala Ile Val Ser Lys
    210                 215                 220

Gly Ile Asp Leu Lys Gly Ser Met Lys Ile Ile Leu Ser Val Pro Gly
225                 230                 235                 240

Leu Leu Ala Leu Val Leu Phe Thr Ser Phe Asn Asn Leu Ile Gly Gly
                245                 250                 255

Val Tyr Ser Ala Leu Met Asp Pro Tyr Gly Leu Glu Leu Phe Ser Pro
```

```
              260                 265                 270
Gln Leu Trp Gly Leu Leu Gly Leu Thr Ser Leu Gly Phe Ile Val
        275                 280                 285
Gly Gly Ala Val Ile Ser Lys Thr Gly Leu Gly Lys Asn Pro Val Arg
        290                 295                 300
Thr Leu Leu Val Asn Val Gly Val Ala Phe Val Gly Met Leu Phe
305                 310                 315                 320
Ala Ile Arg Glu Trp Trp Trp Leu Tyr Ile Leu Gly Ile Phe Ile Phe
                325                 330                 335
Met Ala Ile Thr Pro Ala Ala Glu Ala Ala Glu Gln Thr Ile Leu Gln
            340                 345                 350
Arg Val Val Pro Phe Arg Gln Gln Gly Arg Val Phe Gly Leu Ala Met
        355                 360                 365
Ala Val Glu Met Ala Ala Asn Pro Leu Ser Thr Val Ile Val Ala Ile
        370                 375                 380
Leu Ala Glu Ala Tyr Leu Ile Pro Trp Met Ala Gly Pro Gly Ala Asp
385                 390                 395                 400
Thr Ile Trp Gly Val Ile Leu Gly Glu Gly Lys Ala Arg Gly Met Ala
                405                 410                 415
Leu Met Phe Leu Ala Ser Gly Ala Ile Met Leu Val Val Leu Leu
            420                 425                 430
Ala Phe Met Ser Arg Ser Tyr Arg Lys Leu Ser Gln Tyr Tyr Ala Thr
        435                 440                 445
Thr Ser Gln Asp Ile Ala Gly Ala Ala Glu Lys
    450                 455

<210> SEQ ID NO 11
<211> LENGTH: 3380
<212> TYPE: DNA
<213> ORGANISM: Corynebacterium glutamicum ATCC14067
<220> FEATURE:
<221> NAME/KEY: misc_feature
<222> LOCATION: (1)..(3380)
<223> OTHER INFORMATION: nucleotide sequence comprising locus_tag
      KIQ_001800 disclosed in GenBank accession number AGQQ02000001
<220> FEATURE:
<221> NAME/KEY: misc_feature
<222> LOCATION: (1)..(1000)
<223> OTHER INFORMATION: nucleotide sequence upstream of cds
<220> FEATURE:
<221> NAME/KEY: CDS
<222> LOCATION: (1001)..(2377)
<220> FEATURE:
<221> NAME/KEY: misc_feature
<222> LOCATION: (2378)..(2380)
<223> OTHER INFORMATION: stop codon
<220> FEATURE:
<221> NAME/KEY: misc_feature
<222> LOCATION: (2378)..(3380)
<223> OTHER INFORMATION: nucleotide sequence downstream of cds

<400> SEQUENCE: 11
agccccgagc ctaggcgtaa atgtgaccaa gcgcagcgcg acataaccct aaccagcata    60
agacatcgaa acttccccta ccattcacat tggtaacccg ttggggtgcg tacgctaagt   120
attttaacgc caaccgctcg tgaggtaatc ggcttcctca acatgtggaa ggctgtgtag   180
atcaataact aattgcacgg gtgccacaaa attcaacctg tcctgggtgt aacttcccac   240
caattccgtg gccgttgcgg gcaggagaat gagatcggca tcttctgcca catcaacaat   300
ggtgcccagc gctgagacat caagatcgtg ggcaggttcg tgccacacaa tcgaattccc   360
cagcacaatt tgccccatga tcaccgtggc agccgcagcg cccgacagcg cccatttggt   420
```

```
tttgtgctgt tggaaaagct ccggtagctc agcgatgccg cgtggattga gtttcacaaa    480
ctgcgcatcc tggcgatgtg tgatgccctg aagcgttccg gcttcagaga caagggtgag    540
cggatcgttg atattccacc gctcaaaacg gtgcaaccaa gcgagaatgt cctggttgtg    600
gggattttcg gggacggagg cgtcgataag cgtgcgcgct gcagcggccg caaagggatc    660
gcaggcgtgg tgcgcggcga ccttaatatc aagcccgagc gccaacgcga cctcacgcag    720
cgtcgacagg gtgggctcac tggtgccatc gccgacccgc ttcagggtcg agcgtgagac    780
accggaacgc ctggagatgc gagtgggttg ctccgcggcg agagcaatca attcatcgat    840
cttcacaaca aaccatgcta atcatcacgg ttttcgctc aggcaccggc caacgctttt     900
cgacgcgccc ctccaccttt tcagtagcgt cacgggcgcc aatcctgtat ttttagcagc    960
agtttgaggg ttttgctcc ccatctttag gagacacccc gtg tcc acg ttt cat      1015
                                              Met Ser Thr Phe His
                                                1               5 aaa gtt ctg atc aac acc atg atc tcc aac gtc acc act gga ttt ctg    1063
Lys Val Leu Ile Asn Thr Met Ile Ser Asn Val Thr Thr Gly Phe Leu
              10                  15                  20 ttc ttt gcc gtg gtg ttt tgg atg tat ctt tcc acc ggc aac gtc gca    1111
Phe Phe Ala Val Val Phe Trp Met Tyr Leu Ser Thr Gly Asn Val Ala
             25                  30                  35 ctg acc ggc atc gtc agt gga att tac atg ggt ttg atc gcc gtt tgt    1159
Leu Thr Gly Ile Val Ser Gly Ile Tyr Met Gly Leu Ile Ala Val Cys
         40                  45                  50 tcc atc ttt ttc gga acc gtt gtt gat cac aac cgc aag aaa tcc gtc    1207
Ser Ile Phe Phe Gly Thr Val Val Asp His Asn Arg Lys Lys Ser Val
     55                  60                  65 atg ctg ttt tcc agc gtc acc aca ctc gtg ttt tat tgc ctc agc gca    1255
Met Leu Phe Ser Ser Val Thr Thr Leu Val Phe Tyr Cys Leu Ser Ala
 70                  75                  80                  85 ctg gtg tgg gtg ttt tgg ctg gag gaa gac ggc ctg agc atc gga aat    1303
Leu Val Trp Val Phe Trp Leu Glu Glu Asp Gly Leu Ser Ile Gly Asn
                 90                  95                 100 acc gca ctg tgg gtg ttc gtt tct ttc atc ctc atc ggg tca atc gtg    1351
Thr Ala Leu Trp Val Phe Val Ser Phe Ile Leu Ile Gly Ser Ile Val
            105                 110                 115 gaa cac atg cgc aac atc gcg ctg tcc aca gtg gtc act ttg ctg gtt    1399
Glu His Met Arg Asn Ile Ala Leu Ser Thr Val Val Thr Leu Leu Val
        120                 125                 130 cct gaa gct gaa cgt gac aaa gca aac ggc ctg gta gga gcc gtg caa    1447
Pro Glu Ala Glu Arg Asp Lys Ala Asn Gly Leu Val Gly Ala Val Gln
    135                 140                 145 ggt gtt gga ttt tta gtc acc agt gtc att gct ggt tcc gcg atc ggg    1495
Gly Val Gly Phe Leu Val Thr Ser Val Ile Ala Gly Ser Ala Ile Gly
150                 155                 160                 165 ttc ttg ggc atg gaa atc acc ctg tgg atc tgc ctt ggg ctc tca ctt    1543
Phe Leu Gly Met Glu Ile Thr Leu Trp Ile Cys Leu Gly Leu Ser Leu
                170                 175                 180 gtc gcg ctg ctg cat ctg ctg ccg att cgc atc gac gaa ccg gaa atc    1591
Val Ala Leu Leu His Leu Leu Pro Ile Arg Ile Asp Glu Pro Glu Ile
            185                 190                 195 atc acc caa gaa gac gca cag cct act gtt tct gac gat tca gtt ccc    1639
Ile Thr Gln Glu Asp Ala Gln Pro Thr Val Ser Asp Asp Ser Val Pro
        200                 205                 210 aca cct acc tcc gat ttg gca atc gtg tcc aaa ggc att gac ctt aaa    1687
Thr Pro Thr Ser Asp Leu Ala Ile Val Ser Lys Gly Ile Asp Leu Lys
    215                 220                 225
```

```
gga tca atg aaa atc atc ctg agt gtt ccg gga ctg ctc gcg ctt gtg    1735
Gly Ser Met Lys Ile Ile Leu Ser Val Pro Gly Leu Leu Ala Leu Val
230             235                 240                 245 ttg ttt gcg tcc ttc aac aac ctc atc ggc ggc gtg tac tcc gca ctc    1783
Leu Phe Ala Ser Phe Asn Asn Leu Ile Gly Gly Val Tyr Ser Ala Leu
                250                 255                 260 atg gac cct tac ggc ctg gaa ctt ttc agc cca cag ctg tgg ggg cta    1831
Met Asp Pro Tyr Gly Leu Glu Leu Phe Ser Pro Gln Leu Trp Gly Leu
            265                 270                 275 ctg ctt gga ctc acc agc ctc ggc ttc atc gtt ggt ggt gct gtg atc    1879
Leu Leu Gly Leu Thr Ser Leu Gly Phe Ile Val Gly Gly Ala Val Ile
        280                 285                 290 tcc aaa act ggc ttg ggc aaa aac cct gtg cgc acc ttg ttg ctg gtt    1927
Ser Lys Thr Gly Leu Gly Lys Asn Pro Val Arg Thr Leu Leu Leu Val
    295                 300                 305 aat gtt ggc gtg gct ttt gtt ggc atg tta ttt gcc atc cgc gaa tgg    1975
Asn Val Gly Val Ala Phe Val Gly Met Leu Phe Ala Ile Arg Glu Trp
310                 315                 320                 325 tgg tgg ctc tac atc ctg gga att ttc atc ttc atg gct atc acc cca    2023
Trp Trp Leu Tyr Ile Leu Gly Ile Phe Ile Phe Met Ala Ile Thr Pro
                330                 335                 340 gct gcc gaa gcc gca gaa caa acc atc ctt caa cga gtc gtc cca ttc    2071
Ala Ala Glu Ala Ala Glu Gln Thr Ile Leu Gln Arg Val Val Pro Phe
            345                 350                 355 cgc caa caa gga cgc gta ttt gga tta gcc atg gcg gta gaa atg gca    2119
Arg Gln Gln Gly Arg Val Phe Gly Leu Ala Met Ala Val Glu Met Ala
        360                 365                 370 gcc aac ccg ctg tcc aca gtg atc gtg gcg att ttg gcc gaa gcc tac    2167
Ala Asn Pro Leu Ser Thr Val Ile Val Ala Ile Leu Ala Glu Ala Tyr
    375                 380                 385 ctc atc ccg tgg atg gca ggc ccc ggc gcg gac acc atc tgg ggc gtc    2215
Leu Ile Pro Trp Met Ala Gly Pro Gly Ala Asp Thr Ile Trp Gly Val
390                 395                 400                 405 att ctc ggc gat ggt aaa gct cgc ggc atg gca ctg atg ttc ctc gca    2263
Ile Leu Gly Asp Gly Lys Ala Arg Gly Met Ala Leu Met Phe Leu Ala
                410                 415                 420 tca ggt gcc atc atg ttg gtt gtc gtg ctg ttg gca ttc atg tcg agg    2311
Ser Gly Ala Ile Met Leu Val Val Val Leu Leu Ala Phe Met Ser Arg
            425                 430                 435 tcc tac cgg aaa ctc agc cag tac tac gcc acc acc agc caa gac att    2359
Ser Tyr Arg Lys Leu Ser Gln Tyr Tyr Ala Thr Thr Ser Gln Asp Ile
        440                 445                 450 gcg gga gct gct gag aaa taagttcctg ttagagcgcc ctgaaaatta           2407
Ala Gly Ala Ala Glu Lys
    455 cccCttgagc gtgcagatca tcgagcaaga tctccaaacc atgcgacggt gaatcggggg  2467 caatattgac agttagcatt tctgacatgg gggcttccac gtatagcccc agtgtttcta  2527 gttgggctcg cacctgatca gcagcgatgg catcaacaag cacccggagg gttttgtttc  2587 cgccagcaac tgctacttct tgaaattcca gaacctcatc aacatggtgt gcccgcacga  2647 cgtcgcccag ggcacaatcc tgggcgacag ccggcaagga ggatacgagg tagtagccct  2707 cggcaagcag ttccacgcct acctcttctg attccactcc cggaatatcg agaggaatgc  2767 gcagcttttc ctgcttgccc acgagccgtt agaccgccct ggaaacgtcg agcttctggc  2827 cgccgtcggc gacgtcgaca agcacaccat cgccatcacg gacgttgcct gccagcagtt  2887 ccttagccaa agtatcaccg atggcctgct ggatcagcct cgcaacgga cgagcaccat   2947 aagcagggtc gtagccacgc tccgccagcc aagccttcgc gctgtcgctg actcgaaggt  3007
```

```
taagcctgcg gccagccaaa cggtcagtca gctgcttgat ctggatatca acgatgctgg   3067
tcagctgctc aggggacaaa cgatcgaaga tcacaacatc atcgagacgg ttcacgaact   3127
caggcttgaa tgccatcttc acagcatcca tcatttgttc gcgagtaccg cctgcgccca   3187
ggttagaggt gaggatcaag atggtgttgc ggaaatccac ggtccggcct tggccgtcgg   3247
tgaggcgacc ctcgtcgaga acctgcagga ggatatcgaa gacatcaggg tgagccttct   3307
ccacctcgtc gaaaagcacg acggtgtacg gacgacggcg cactgcctca gtgagctgac   3367
cgccctggtc ata                                                      3380
```

<210> SEQ ID NO 12
<211> LENGTH: 459
<212> TYPE: PRT
<213> ORGANISM: Corynebacterium glutamicum ATCC14067

<400> SEQUENCE: 12

```
Met Ser Thr Phe His Lys Val Leu Ile Asn Thr Met Ile Ser Asn Val
  1               5                  10                  15

Thr Thr Gly Phe Leu Phe Phe Ala Val Val Phe Trp Met Tyr Leu Ser
             20                  25                  30

Thr Gly Asn Val Ala Leu Thr Gly Ile Val Ser Gly Ile Tyr Met Gly
         35                  40                  45

Leu Ile Ala Val Cys Ser Ile Phe Phe Gly Thr Val Val Asp His Asn
     50                  55                  60

Arg Lys Lys Ser Val Met Leu Phe Ser Ser Val Thr Thr Leu Val Phe
 65                  70                  75                  80

Tyr Cys Leu Ser Ala Leu Val Trp Val Phe Trp Leu Glu Glu Asp Gly
                 85                  90                  95

Leu Ser Ile Gly Asn Thr Ala Leu Trp Val Phe Val Ser Phe Ile Leu
            100                 105                 110

Ile Gly Ser Ile Val Glu His Met Arg Asn Ile Ala Leu Ser Thr Val
        115                 120                 125

Val Thr Leu Leu Val Pro Glu Ala Glu Arg Asp Lys Ala Asn Gly Leu
    130                 135                 140

Val Gly Ala Val Gln Gly Val Gly Phe Leu Val Thr Ser Val Ile Ala
145                 150                 155                 160

Gly Ser Ala Ile Gly Phe Leu Gly Met Glu Ile Thr Leu Trp Ile Cys
                165                 170                 175

Leu Gly Leu Ser Leu Val Ala Leu Leu His Leu Leu Pro Ile Arg Ile
            180                 185                 190

Asp Glu Pro Glu Ile Ile Thr Gln Glu Asp Ala Gln Pro Thr Val Ser
        195                 200                 205

Asp Asp Ser Val Pro Thr Pro Thr Ser Asp Leu Ala Ile Val Ser Lys
    210                 215                 220

Gly Ile Asp Leu Lys Gly Ser Met Lys Ile Ile Leu Ser Val Pro Gly
225                 230                 235                 240

Leu Leu Ala Leu Val Leu Phe Ala Ser Phe Asn Asn Leu Ile Gly Gly
                245                 250                 255

Val Tyr Ser Ala Leu Met Asp Pro Tyr Gly Leu Glu Leu Phe Ser Pro
            260                 265                 270

Gln Leu Trp Gly Leu Leu Leu Gly Leu Thr Ser Leu Gly Phe Ile Val
        275                 280                 285

Gly Gly Ala Val Ile Ser Lys Thr Gly Leu Gly Lys Asn Pro Val Arg
    290                 295                 300
```

Thr Leu Leu Leu Val Asn Val Gly Val Ala Phe Val Gly Met Leu Phe
305                 310                 315                 320

Ala Ile Arg Glu Trp Trp Leu Tyr Ile Leu Gly Ile Phe Ile Phe
            325                 330                 335

Met Ala Ile Thr Pro Ala Ala Glu Ala Ala Glu Gln Thr Ile Leu Gln
        340                 345                 350

Arg Val Val Pro Phe Arg Gln Gln Gly Arg Val Phe Gly Leu Ala Met
            355                 360                 365

Ala Val Glu Met Ala Ala Asn Pro Leu Ser Thr Val Ile Val Ala Ile
        370                 375                 380

Leu Ala Glu Ala Tyr Leu Ile Pro Trp Met Ala Gly Pro Gly Ala Asp
385                 390                 395                 400

Thr Ile Trp Gly Val Ile Leu Gly Asp Gly Lys Ala Arg Gly Met Ala
            405                 410                 415

Leu Met Phe Leu Ala Ser Gly Ala Ile Met Leu Val Val Val Leu Leu
            420                 425                 430

Ala Phe Met Ser Arg Ser Tyr Arg Lys Leu Ser Gln Tyr Tyr Ala Thr
        435                 440                 445

Thr Ser Gln Asp Ile Ala Gly Ala Ala Glu Lys
    450                 455

<210> SEQ ID NO 13
<211> LENGTH: 1606
<212> TYPE: DNA
<213> ORGANISM: artificial sequence
<220> FEATURE:
<223> OTHER INFORMATION: nucleotide sequence comprising a deletion of
      the cds of the cmr gene of Corynebacterium glutamicum and the
      adjoining stop codon accompanied by insertion of the recognition
      site for restriction endonuclease EcoRV
<220> FEATURE:
<221> NAME/KEY: misc_feature
<222> LOCATION: (1)..(800)
<223> OTHER INFORMATION: nucleotide sequence of ATCC13032 upstream
      (5'-flanking sequence) of sequence coding for Cmr polypeptide
<220> FEATURE:
<221> NAME/KEY: misc_feature
<222> LOCATION: (801)..(806)
<223> OTHER INFORMATION: artificially inserted recognition site for
      restriction endonuclease EcoRV
<220> FEATURE:
<221> NAME/KEY: misc_feature
<222> LOCATION: (807)..(1606)
<223> OTHER INFORMATION: nucleotide sequence of ATCC13032 downstream
      (3'-flanking sequence) of sequence coding for Cmr polypeptide

<400> SEQUENCE: 13
gtgccacaaa atttagcctg tcctgggtgt aacttcccac cagttccgtg accgttgcgg      60
gcaggagaat tagatcggcg tcttctgcca catcaacaat ggtgcccagc gctgagacat     120
cgagatcgtg ggcaggttcg tgccacacaa tcgaattccc cagcacaatt tgtcccatga     180
tcaccgtggc agccgcagcg cccgacagcc cccatttggt tttgtgctgt tggaaaagct     240
ccggtagctc agcgatgccg cgtggattga gtttcacaaa ctgcgcatcc tggcgatgtg     300
tgatgccctg aagcgttccg gcttcagaga caagggtgag cggatcgttg atattccacc     360
gctcaaaacg gtgcaaccaa gcgagaattt cctggttgtg gggattttcg gggacggagg     420
cgtcgataag cgtgcgcgct gcagcggccg caaagggatc gcaggcgtgg tgcgcggcga     480
ccttaatatc aagcccgagc gccaacgcga cctcacgcag cgtcgacagg gtgggctcgc     540
tggtgccatc gccgacccgc ttcagggtcg agcgcgagac accggaacgc ctggagatgc     600

-continued

```
gagtgggttg ctccgcggcg agagcaatca attcatcgat cttcacaaca aaccatgcta    660
atcatcacgg tttttcgctc aggcaccggc caacgctttt cgacgcgccc ctccaccttt    720
tcagtagcgt cacgggcgcc aatcctgtat ttttagcagc agtttgaggg ttttgctcc     780 ccatctttag gagacacccc gatatcgtgc tctagaccgt tgtttgattg gcttttcttg    840
cctgttgaac gagggaaaga aaacaaaca gtcctgaagc tacacccaaa gaagcagcat     900
aaattggttc cgcagggaac ccattggcaa caaaacacaa gataatcatt gcgccaactt    960
gccaaaccgg ggcccgcttt ttccaaaatc gaactgtgga gaatttatta atccccatg    1020 acaaggcaac aaggaggccg atgaaagcta tggctaaaag aacttgattc agagttagcg   1080
agtaaatgaa caatccaaaa aaacatagaa gcgataaaac tctgccagta catattcacc   1140
ttgagaggct ttgggtatcg gtagtcaact gatacagagg gatctattaa gtacatttaa   1200
gagtacttca ctttgaatcg ttgttctggg attctctcaa ccccgggcct aaaacgtcag   1260
ctctctacaa ttaggcgctc tataacgccc tgaaaattac cccctgagca tgcagatcat   1320
cgagcaggat ctccaaaccg tgcgacggtg aatcggggc aatattgaca gttagcattt    1380
ctgacatggg agcttccacg tgtagcccaa gtgtttctag ttgggctcgc acgtggtcag   1440
cagcgatggc atcaacgagc acccggaggg ttttgtttcc gccagcaact gcccacttct   1500
gaaattccaa gacctcatca acatgatgtg cccgcacgac gtcacccagg gcacagtcct   1560
gggcgacagc cggcaaagtg gctaccaggt agtagccttc ggcaag               1606
```

<210> SEQ ID NO 14
<211> LENGTH: 1266
<212> TYPE: DNA
<213> ORGANISM: Corynebacterium glutamicum ATCC13032
<220> FEATURE:
<221> NAME/KEY: CDS
<222> LOCATION: (1)..(1263)
<223> OTHER INFORMATION: nucleotide sequence encoding aspartokinase
<220> FEATURE:
<221> NAME/KEY: misc_feature
<222> LOCATION: (1264)..(1266)
<223> OTHER INFORMATION: stop codon

<400> SEQUENCE: 14

```
gtg gcc ctg gtc gta cag aaa tat ggc ggt tcc tcg ctt gag agt gcg       48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct       96
Glu Arg Ile Arg Asn Val Ala Glu Arg Ile Val Ala Thr Lys Lys Ala
                20                  25                  30 gga aat gat gtc gtg gtt gtc tgc tcc gca atg gga gac acc acg gat      144
Gly Asn Asp Val Val Val Val Cys Ser Ala Met Gly Asp Thr Thr Asp
            35                  40                  45 gaa ctt cta gaa ctt gca gcg gca gtg aat ccc gtt ccg cca gct cgt      192
Glu Leu Leu Glu Leu Ala Ala Ala Val Asn Pro Val Pro Pro Ala Arg
        50                  55                  60 gaa atg gat atg ctc ctg act gct ggt gag cgt att tct aac gct ctc      240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg      288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc      336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc      384
```

```
                Ile Val Asp Val Thr Pro Gly Arg Val Arg Glu Ala Leu Asp Glu Gly
                    115                 120                 125 aag atc tgc att gtt gct ggt ttc cag ggt gtt aat aaa gaa acc cgc           432
Lys Ile Cys Ile Val Ala Gly Phe Gln Gly Val Asn Lys Glu Thr Arg
130                 135                 140 gat gtc acc acg ttg ggt cgt ggt ggt tct gac acc act gca gtt gcg           480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt           528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag           576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc           624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat           672
Ser Lys Ile Leu Val Leu Arg Ser Val Glu Tyr Ala Arg Ala Phe Asn
210                 215                 220 gtg cca ctt cgc gta cgc tcg tct tat agt aat gat ccc ggc act ttg           720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc           768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att           816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat           864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa           912
Ala Glu Ile Asn Ile Asp Met Val Leu Gln Asn Val Ser Ser Val Glu
290                 295                 300 gac ggc acc acc gac atc acc ttc acc tgc cct cgt tcc gac ggc cgc           960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc          1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct          1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg          1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt          1152
Arg Asp Val Asn Val Asn Ile Glu Leu Ile Ser Thr Ser Glu Ile Arg
370                 375                 380 att tcc gtg ctg atc cgt gaa gat gat ctg gat gct gct gca cgt gca          1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat          1248
Leu His Glu Gln Phe Gln Leu Gly Gly Glu Asp Glu Ala Val Val Tyr
                405                 410                 415 gca ggc acc gga cgc taa                                                  1266
Ala Gly Thr Gly Arg
            420
```

<210> SEQ ID NO 15
<211> LENGTH: 421
<212> TYPE: PRT
<213> ORGANISM: Corynebacterium glutamicum ATCC13032

<400> SEQUENCE: 15

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380
```

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 16
<211> LENGTH: 43
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(43)
<223> OTHER INFORMATION: primer 1f-Dcmr

<400> SEQUENCE: 16
agctcggtac ccggggatcc tgtgccacaa aatttagcct gtc          43

<210> SEQ ID NO 17
<211> LENGTH: 46
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(46)
<223> OTHER INFORMATION: primer 1r-Dcmr

<400> SEQUENCE: 17
caaacaacgg tctagagcac gatatcgggg tgtctcctaa agatgg       46

<210> SEQ ID NO 18
<211> LENGTH: 46
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(46)
<223> OTHER INFORMATION: primer 2f-Dcmr

<400> SEQUENCE: 18
ccatctttag gagacacccc gatatcgtgc tctagaccgt tgtttg       46

<210> SEQ ID NO 19
<211> LENGTH: 41
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(41)
<223> OTHER INFORMATION: primer 2r-Dcmr

<400> SEQUENCE: 19
tgcatgcctg caggtcgact cttgccgaag gctactacct g            41

<210> SEQ ID NO 20
<211> LENGTH: 847
<212> TYPE: DNA
<213> ORGANISM: artificial sequence

```
<220> FEATURE:
<223> OTHER INFORMATION: amplificate cmr_up
<220> FEATURE:
<221> NAME/KEY: misc_feature
<222> LOCATION: (1)..(21)
<223> OTHER INFORMATION: 5'-overlap to pK18mobsacB cut by XbaI
<220> FEATURE:
<221> NAME/KEY: misc_feature
<222> LOCATION: (22)..(821)
<223> OTHER INFORMATION: sequence corresponding to the sequence of
      SEQ ID NO:7 positions 201 to 1000
<220> FEATURE:
<221> NAME/KEY: misc_feature
<222> LOCATION: (802)..(847)
<223> OTHER INFORMATION: 3'-overlap to amplificate cmr_down
<220> FEATURE:
<221> NAME/KEY: misc_feature
<222> LOCATION: (822)..(827)
<223> OTHER INFORMATION: recognition site for restriction endonuclease
      EcoRV

<400> SEQUENCE: 20
agctcggtac ccggggatcc tgtgccacaa aatttagcct gtcctgggtg taacttccca       60
ccagttccgt gaccgttgcg ggcaggagaa ttagatcggc gtcttctgcc acatcaacaa      120
tggtgcccag cgctgagaca tcgagatcgt gggcaggttc gtgccacaca atcgaattcc      180
ccagcacaat ttgtcccatg atcaccgtgg cagccgcagc gcccgacagc gcccatttgg      240
ttttgtgctg ttggaaaagc tccggtagct cagcgatgcc gcgtggattg agtttcacaa      300
actgcgcatc ctggcgatgt gtgatgccct gaagcgttcc ggcttcagag acaagggtga      360
gcggatcgtt gatattccac cgctcaaaac ggtgcaacca agcgagaatt tcctggttgt      420
ggggattttc ggggacggag gcgtcgataa gcgtgcgcgc tgcagcggcc gcaaagggat      480
cgcaggcgtg gtgcgcggcg accttaatat caagcccgag cgccaacgcg acctcacgca      540
gcgtcgacag ggtgggctcg ctggtgccat cgccgacccg cttcagggtc gagcgcgaga      600
caccggaacg cctggagatg cgagtgggtt gctccgcggc gagagcaatc aattcatcga      660
tcttcacaac aaaccatgct aatcatcacg gttttttcgct caggcaccgg ccaacgcttt      720
tcgacgcgcc cctccacctt ttcagtagcg tcacgggcgc caatcctgta tttttagcag      780
cagtttgagg gttttttgctc cccatcttta ggagacaccc cgatatcgtg ctctagaccg      840
ttgtttg                                                                847

<210> SEQ ID NO 21
<211> LENGTH: 846
<212> TYPE: DNA
<213> ORGANISM: artificial sequence
<220> FEATURE:
<223> OTHER INFORMATION: amplificate cmr_down
<220> FEATURE:
<221> NAME/KEY: misc_feature
<222> LOCATION: (1)..(46)
<223> OTHER INFORMATION: 5'-overlap to amplificate cmr_up
<220> FEATURE:
<221> NAME/KEY: misc_feature
<222> LOCATION: (21)..(26)
<223> OTHER INFORMATION: reccognition site for restriction endonuclease
      EcoRV
<220> FEATURE:
<221> NAME/KEY: misc_feature
<222> LOCATION: (27)..(826)
<223> OTHER INFORMATION: sequence corresponding to the sequence of
      SEQ ID NO:7 positions 2381 to 3180
<220> FEATURE:
<221> NAME/KEY: misc_feature
<222> LOCATION: (827)..(846)
<223> OTHER INFORMATION: 3'-overlap to pK18mobsacB cut by XbaI
```

<400> SEQUENCE: 21

```
ccatctttag gagacacccc gatatcgtgc tctagaccgt tgtttgattg gcttttcttg    60
cctgttgaac gagggaaaga aaacaaaca gtcctgaagc tacacccaaa gaagcagcat   120
aaattggttc cgcagggaac ccattggcaa caaaacacaa gataatcatt gcgccaactt   180
gccaaaccgg ggcccgcttt ttccaaaatc gaactgtgga gaatttatta atcccccatg   240
acaaggcaac aaggaggccg atgaaagcta tggctaaaag aacttgattc agagttagcg   300
agtaaatgaa caatccaaaa aaacatagaa gcgataaaac tctgccagta catattcacc   360
ttgagaggct ttgggtatcg gtagtcaact gatacagagg gatctattaa gtacatttaa   420
gagtacttca ctttgaatcg ttgttctggg attctctcaa ccccgggcct aaaacgtcag   480
ctctctacaa ttaggcgctc tataacgccc tgaaaattac ccctgagca tgcagatcat   540
cgagcaggat ctccaaaccg tgcgacggtg aatcggggc aatattgaca gttagcattt   600
ctgacatggg agcttccacg tgtagcccaa gtgtttctag ttgggctcgc acgtggtcag   660
cagcgatggc atcaacgagc acccggaggg ttttgtttcc gccagcaact gccacttctt   720
gaaattccaa gacctcatca acatgatgtg cccgcacgac gtcacccagg gcacagtcct   780
gggcgacagc cggcaaagtg gctaccaggt agtagccttc ggcaagagtc gacctgcagg   840
catgca                                                               846
```

<210> SEQ ID NO 22
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer pCV22_1.p

<400> SEQUENCE: 22

```
aggtttcccg actggaaagc                                                 20
```

<210> SEQ ID NO 23
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer pCV22_2.p

<400> SEQUENCE: 23

```
tgcaaggcga ttaagttggg                                                 20
```

<210> SEQ ID NO 24
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(23)
<223> OTHER INFORMATION: primer pVW_1.p

<400> SEQUENCE: 24

```
gtgagcggat aacaatttca cac                                             23
```

```
<210> SEQ ID NO 25
<211> LENGTH: 16
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(16)
<223> OTHER INFORMATION: primer M13For

<400> SEQUENCE: 25
gtaaaacgac ggccag                                              16

<210> SEQ ID NO 26
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer NCgl2679_fw

<400> SEQUENCE: 26
ctggagatgc gagtgggttg                                          20

<210> SEQ ID NO 27
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer NCgl2679_rev

<400> SEQUENCE: 27
tgctgcttct ttgggtgtag                                          20

<210> SEQ ID NO 28
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer NCgl2679_fwd1

<400> SEQUENCE: 28
tagcctgtcc tgggtgtaac                                          20

<210> SEQ ID NO 29
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer NCgl2681_rev1

<400> SEQUENCE: 29
```

```
cgtgcgggca catcatgttg                                               20
```

<210> SEQ ID NO 30
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer NCgl2679_fwd2

<400> SEQUENCE: 30

```
tcgagatcgt gggcaggttc                                               20
```

<210> SEQ ID NO 31
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer NCgl2681_rev2

<400> SEQUENCE: 31

```
cgtggaagct cccatgtcag                                               20
```

<210> SEQ ID NO 32
<211> LENGTH: 1181
<212> TYPE: DNA
<213> ORGANISM: Corynebacterium glutamicum DM1933_deltacmr::EcoRV
<220> FEATURE:
<221> NAME/KEY: misc_feature
<222> LOCATION: (1)..(1181)
<223> OTHER INFORMATION: sequence displayed in SEQ ID NO:13 positions
      168 to 1348
<220> FEATURE:
<221> NAME/KEY: misc_feature
<222> LOCATION: (634)..(639)
<223> OTHER INFORMATION: recognition site for restriction endonuclease
      EcoRV

<400> SEQUENCE: 32

```
atttgtccca tgatcaccgt ggcagccgca gcgcccgaca gcgcccattt ggttttgtgc    60
tgttggaaaa gctccggtag ctcagcgatg ccgcgtggat tgagtttcac aaactgcgca   120
tcctggcgat gtgtgatgcc ctgaagcgtt ccggcttcag agacaagggt gagcggatcg   180
ttgatattcc accgctcaaa acggtgcaac caagcgagaa tttcctggtt gtggggattt   240
tcggggacgg aggcgtcgat aagcgtgcgc gctgcagcgg ccgcaaaggg atcgcaggcg   300
tggtgcgcgg cgaccttaat atcaagcccg agcgccaacg cgacctcacg cagcgtcgac   360
agggtgggct cgctggtgcc atcgccgacc cgcttcaggg tcgagcgcga cacaccggaa   420
cgcctggaga tgcgagtggg ttgctccgcg gcgagagcaa tcaattcatc gatcttcaca   480
acaaaccatg ctaatcatca cggttttttcg ctcaggcacc ggccaacgct tttcgacgcg   540
cccctccacc ttttcagtag cgtcacgggc gccaatcctg tattttagc agcagtttga    600 gggttttgc tccccatctt taggagacac cccgatatcg tgctctagac cgttgtttga    660
ttggcttttc ttgcctgttg aacgagggaa agaaaaacaa acagtcctga agctacaccc   720
aaagaagcag cataaattgg ttccgcaggg aacccattgg caacaaaaca caagataatc   780
attgcgccaa cttgccaaac cggggcccgc ttttttccaaa atcgaactgt ggagaattta   840
```

```
ttaatccccc atgacaaggc aacaaggagg ccgatgaaag ctatggctaa aagaacttga    900
ttcagagtta gcgagtaaat gaacaatcca aaaaaacata gaagcgataa aactctgcca    960
gtacatattc accttgagag gctttgggta tcggtagtca actgatacag agggatctat   1020
taagtacatt taagagtact tcactttgaa tcgttgttct gggattctct caacccgggg   1080
cctaaaacgt cagctctcta caattaggcg ctctataacg ccctgaaaat taccccctga   1140
gcatgcagat catcgagcag gatctccaaa ccgtgcgacg g                       1181
```

What is claimed is:

1. A bacterium of the genus *Corynebacterium*, wherein:
   a) the bacterium has the ability to excrete an L-amino acid selected from proteinogenic L-amino acids and L-ornithine;
   b) the bacterium comprises a chromosome with a polynucleotide that, prior to modification, encodes a polypeptide which is at least 90% identical to the amino acid sequence of SEQ ID NO:8 and which confers upon *Escherichia coli* a resistance to at least one antibiotic, selected from erythromycin, tetracycline, puromycin and bleomycin; and
   c) said chromosome has been modified by a modification comprising either:
      i) a deletion of part or all of the polynucleotide sequence coding for a portion of the polypeptide corresponding to amino acids 149 to 251, 41 to 344, or 14 to 435 of SEQ ID NO:8; or
      ii) a deletion of the complete polynucleotide sequence coding for said polypeptide.

2. The bacterium of claim 1, wherein the modification comprises a deletion of at least the complete nucleotide sequence coding for said polypeptide and the adjoining stop codon.

3. The bacterium of claim 1, wherein the modification further comprises an insertion of a recognition site for the restriction enzyme EcoRV.

4. The bacterium of claim 1, wherein said bacterium belongs to the species *Corynebacterium glutamicum*.

5. The bacterium of claim 1, wherein said L-amino acid is selected from the proteinogenic L-amino acids L-lysine, L-valine, L-threonine, L-isoleucine, L-histidine and L-proline.

6. The bacterium of claim 5, wherein said L-amino acid is L-lysine.

7. The bacterium of claim 1, wherein, prior to modification, the amino acid sequence of the polypeptide comprises 459 amino acids.

8. The bacterium of claim 7, wherein, prior to modification, the polypeptide comprises the amino acid sequence of SEQ ID NO:8 or SEQ ID NO:10 or SEQ ID NO:12 prior.

9. The bacterium of claim 8, wherein prior to modification, the polypeptide comprises the amino acid sequence of SEQ ID NO:8.

10. The bacterium of claim 9, wherein, prior to modification, the nucleotide sequence coding for said polypeptide comprises positions 1001 to 2377 of the nucleotide sequence of SEQ ID NO:7 or positions 1001 to 2377 of SEQ ID NO:7, wherein at position 2341 cytosine (c) is replaced by thymine (t).

11. A method for the fermentative production of an L-amino acid, selected from proteinogenic L-amino acids and L-ornithine, comprising the steps of:
   a) cultivating the bacterium of claim 1 in a medium under conditions suitable for the production of said L-amino acid;
   b) accumulating said L-amino acid in the medium to form an L-amino acid containing fermentation broth.

12. The method of claim 11, wherein said L-amino acid is selected from the proteinogenic L-amino acids L-lysine, L-valine, L-threonine, L-isoleucine, L-histidine and L-proline.

13. The method of claim 12, wherein said L-amino acid is L-lysine.

14. The method of claim 11, further comprising concentration of the L-amino acid containing fermentation broth.

15. The method of claim 11, further comprising drying the L-amino acid containing fermentation broth.

16. The method of claim 11, further comprising purifying the L-amino acid from said L-amino acid containing fermentation broth.

* * * * *